US008057515B2

(12) United States Patent
Flynn et al.

(10) Patent No.: US 8,057,515 B2
(45) Date of Patent: *Nov. 15, 2011

(54) LOAD-SHARING ANCHOR HAVING A DEFLECTABLE POST AND CENTERING SPRING AND METHOD FOR DYNAMIC STABILIZATION OF THE SPINE

(75) Inventors: John J. Flynn, Walnut Creek, CA (US); Charles J. Winslow, Walnut Creek, CA (US); Steven T. Mitchell, Pleasant Hill, CA (US); James F. Zucherman, San Francisco, CA (US); Ken Y. Hsu, San Francisco, CA (US); Henry A. Klyce, Piedmont, CA (US); H. Adam R. Klyce, Berkeley, CA (US)

(73) Assignee: Spartek Medical, Inc., Alameda, CA (US)

( * ) Notice: Subject to any disclaimer, the term of this patent is extended or adjusted under 35 U.S.C. 154(b) by 219 days.
This patent is subject to a terminal disclaimer.

(21) Appl. No.: 12/566,551

(22) Filed: Sep. 24, 2009

(65) Prior Publication Data
US 2010/0030268 A1 Feb. 4, 2010

Related U.S. Application Data

(63) Continuation-in-part of application No. 12/130,395, filed on May 30, 2008, and a continuation-in-part of application No. 12/130,095, filed on May 30, 2008.

(60) Provisional application No. 61/100,593, filed on Sep. 26, 2008, provisional application No. 61/100,625, filed on Sep. 26, 2008, provisional application No. 61/119,651, filed on Dec. 3, 2008, provisional application No. 61/122,658, filed on Dec. 15, 2008, provisional application No. 61/144,426, filed on Jan. 13, 2009, provisional application No. 61/225,478, filed on Jul. 14, 2009, provisional application No. 61/167,789, filed on Apr. 8, 2009, provisional application No. 61/217,556, filed on Jun. 1, 2009, provisional application No. 61/031,598, filed on Feb. 26, 2008, provisional application No. 61/057,340, filed on May 30, 2008.

(51) Int. Cl.
*A61B 17/70* (2006.01)
*A61B 17/86* (2006.01)
(52) U.S. Cl. ........................................ 606/246; 606/305
(58) Field of Classification Search .................. 606/264, 606/305, 308, 302, 257, 254, 260, 279, 246, 606/266
See application file for complete search history.

(56) References Cited

U.S. PATENT DOCUMENTS 4,041,939 A  8/1977  Hall ................................ 128/69
(Continued)

FOREIGN PATENT DOCUMENTS
DE    2649042 B1    10/1976
(Continued)

OTHER PUBLICATIONS

Mekanika, Inc. Website, 2003; Mekanika—The Spinal Stabilization Company, product description for Modulus System, 2 pages, <http://mekanika.com/htm/modsystem.htm>.

(Continued)

*Primary Examiner* — Pedro Philogene
(74) *Attorney, Agent, or Firm* — Fliesler Meyer LLP

(57) ABSTRACT

A dynamic spinal stabilization bone anchor which supports the spine while providing for the preservation of spinal motion. The dynamic bone anchor provides load sharing while preserving range of motion and reducing stress exerted upon the bone anchors and spinal anatomy. The dynamic bone anchor includes a deflectable post connected by a ball-joint to a threaded anchor. Deflection of the deflectable post is controlled by a centering spring. The force/deflection properties of the dynamic bone anchor may be adapted to the anatomy and functional requirements of the patient. The dynamic bone anchor may be used as a component of a dynamic stabilization system which supports the spine while providing for the preservation of spinal motion.

30 Claims, 16 Drawing Sheets

U.S. PATENT DOCUMENTS

| | | | |
|---|---|---|---|
| 4,065,817 A | 1/1978 | Branemark et al. | 3/1.91 |
| 4,274,401 A | 6/1981 | Miskew | |
| 4,347,845 A | 9/1982 | Mayfield | 128/303 |
| 4,369,770 A | 1/1983 | Bacal et al. | 128/69 |
| 4,382,438 A | 5/1983 | Jacobs | 128/69 |
| 4,409,968 A | 10/1983 | Drummond | 128/69 |
| 4,411,259 A | 10/1983 | Drummond | 128/69 |
| 4,422,451 A | 12/1983 | Kalamchi | 128/69 |
| 4,479,491 A | 10/1984 | Martin | 128/92 |
| 4,567,885 A | 2/1986 | Androphy | 128/92 |
| 4,573,454 A | 3/1986 | Hoffman | 128/69 |
| 4,604,995 A | 8/1986 | Stephens et al. | 128/69 |
| 4,611,580 A | 9/1986 | Wu | 128/69 |
| 4,611,581 A | 9/1986 | Steffee | 128/69 |
| 4,611,582 A | 9/1986 | Duff | 128/69 |
| 4,641,636 A | 2/1987 | Cotrel | 128/69 |
| 4,648,388 A | 3/1987 | Steffee | 128/69 |
| 4,653,481 A | 3/1987 | Howland et al. | 128/69 |
| 4,653,489 A | 3/1987 | Tronzo | 128/92 |
| 4,655,199 A | 4/1987 | Steffee | 128/69 |
| 4,658,809 A | 4/1987 | Ulrich et al. | 128/92 |
| 4,696,290 A | 9/1987 | Steffee | 128/69 |
| 4,719,905 A | 1/1988 | Steffee | 128/69 |
| 4,763,644 A | 8/1988 | Webb | 128/69 |
| 4,773,402 A | 9/1988 | Asher et al. | 128/69 |
| 4,805,602 A | 2/1989 | Puno et al. | 128/69 |
| 4,815,453 A | 3/1989 | Cotrel | 128/69 |
| 4,887,595 A | 12/1989 | Heinig et al. | 606/61 |
| 4,913,134 A | 4/1990 | Luque | 128/69 |
| 4,946,458 A | 8/1990 | Harms et al. | 606/61 |
| 4,950,269 A | 8/1990 | Gaines, Jr. | 606/61 |
| 4,955,885 A | 9/1990 | Meyers | 606/53 |
| 4,987,892 A | 1/1991 | Krag et al. | 606/61 |
| 5,005,562 A | 4/1991 | Cotrel | 128/69 |
| 5,024,213 A | 6/1991 | Asher et al. | 128/69 |
| 5,030,220 A | 7/1991 | Howland | 606/61 |
| 5,042,982 A | 8/1991 | Harms et al. | 606/61 |
| 5,047,029 A | 9/1991 | Aebi et al. | 606/61 |
| 5,067,955 A | 11/1991 | Cotrel | 606/61 |
| 5,074,864 A | 12/1991 | Cozad et al. | 606/54 |
| 5,084,049 A | 1/1992 | Asher et al. | 606/61 |
| 5,092,866 A | 3/1992 | Breard et al. | 606/61 |
| 5,102,412 A | 4/1992 | Rogozinski | 606/61 |
| 5,112,332 A | 5/1992 | Cozad et al. | 606/61 |
| 5,113,685 A | 5/1992 | Asher et al. | 72/458 |
| 5,116,334 A | 5/1992 | Cozad et al. | |
| 5,127,912 A | 7/1992 | Ray et al. | 606/61 |
| 5,129,388 A | 7/1992 | Vignaud et al. | 606/61 |
| 5,129,900 A | 7/1992 | Asher et al. | 606/61 |
| 5,147,359 A | 9/1992 | Cozad et al. | 606/61 |
| 5,154,718 A | 10/1992 | Cozad et al. | 606/61 |
| 5,176,680 A | 1/1993 | Vignaud et al. | 606/61 |
| 5,180,393 A | 1/1993 | Commarmond | 623/13 |
| 5,190,543 A | 3/1993 | Schläpfer | 606/61 |
| 5,201,734 A | 4/1993 | Cozad et al. | 606/62 |
| 5,207,678 A | 5/1993 | Harms et al. | 606/61 |
| 5,261,911 A | 11/1993 | Carl | 606/61 |
| 5,261,912 A | 11/1993 | Frigg | 606/61 |
| 5,261,913 A | 11/1993 | Marnay | 606/61 |
| 5,281,222 A | 1/1994 | Allard et al. | 606/54 |
| 5,282,801 A | 2/1994 | Sherman | 606/61 |
| 5,282,863 A | 2/1994 | Burton | 623/17 |
| 5,290,289 A | 3/1994 | Sanders et al. | 606/61 |
| 5,312,402 A | 5/1994 | Schläpfer et al. | 606/53 |
| 5,312,404 A | 5/1994 | Asher et al. | 606/61 |
| 5,344,422 A | 9/1994 | Frigg | 606/61 |
| 5,346,493 A | 9/1994 | Stahurski et al. | 606/61 |
| 5,360,429 A | 11/1994 | Jeanson et al. | 606/61 |
| 5,360,431 A | 11/1994 | Puno et al. | 606/72 |
| 5,374,267 A | 12/1994 | Siegal | |
| 5,380,325 A | 1/1995 | Lahille et al. | 606/61 |
| 5,380,326 A | 1/1995 | Lin | 606/61 |
| 5,382,248 A | 1/1995 | Jacobson et al. | 606/60 |
| 5,385,583 A | 1/1995 | Cotrel | 623/17 |
| 5,387,213 A | 2/1995 | Breard et al. | 606/61 |
| 5,415,661 A | 5/1995 | Holmes | 606/69 |
| 5,429,639 A | 7/1995 | Judet | 606/61 |
| 5,437,672 A | 8/1995 | Alleyne | |
| 5,443,467 A | 8/1995 | Biedermann et al. | 606/65 |
| 5,466,237 A | 11/1995 | Byrd, III et al. | 606/61 |
| 5,474,555 A | 12/1995 | Puno et al. | 606/73 |
| 5,480,442 A | 1/1996 | Bertanoli | |
| 5,487,742 A | 1/1996 | Cotrel | 606/61 |
| 5,496,321 A | 3/1996 | Puno et al. | 606/61 |
| 5,498,264 A | 3/1996 | Schlapfer et al. | 606/72 |
| 5,501,684 A | 3/1996 | Schlapfer et al. | |
| 5,520,689 A | 5/1996 | Schläpfer et al. | 606/61 |
| 5,534,001 A | 7/1996 | Schlapfer et al. | 606/61 |
| 5,536,268 A | 7/1996 | Griss | 606/61 |
| 5,540,688 A | 7/1996 | Navas | 606/61 |
| 5,545,167 A | 8/1996 | Lin | 606/61 |
| 5,549,607 A | 8/1996 | Olson et al. | 606/61 |
| 5,562,737 A | 10/1996 | Graf | 623/17 |
| 5,569,248 A | 10/1996 | Mathews | 606/61 |
| 5,591,166 A | 1/1997 | Bernhardt et al. | |
| 5,601,552 A | 2/1997 | Cotrel | |
| 5,609,592 A | 3/1997 | Brumfield et al. | 606/61 |
| 5,609,593 A | 3/1997 | Errico et al. | 606/61 |
| 5,611,800 A | 3/1997 | Davis et al. | 606/61 |
| 5,624,441 A | 4/1997 | Sherman et al. | 606/61 |
| 5,628,740 A | 5/1997 | Mullane | 606/61 |
| 5,630,816 A | 5/1997 | Kambin | 606/61 |
| 5,643,260 A | 7/1997 | Doherty | 606/61 |
| 5,645,599 A | 7/1997 | Samani | 623/17 |
| 5,651,789 A | 7/1997 | Cotrel | 606/61 |
| 5,653,708 A | 8/1997 | Howland | 606/61 |
| 5,658,284 A | 8/1997 | Sebastian et al. | 606/61 |
| 5,658,285 A | 8/1997 | Marnay et al. | |
| 5,667,506 A | 9/1997 | Sutterlin | 606/61 |
| 5,667,507 A | 9/1997 | Corin et al. | 606/61 |
| 5,669,910 A | 9/1997 | Korhonen et al. | 606/61 |
| 5,672,175 A | 9/1997 | Martin | 606/61 |
| 5,672,176 A | 9/1997 | Biedermann et al. | 606/61 |
| 5,676,665 A | 10/1997 | Bryan | 606/61 |
| 5,676,703 A | 10/1997 | Gelbard | 623/17 |
| 5,681,310 A | 10/1997 | Yuan et al. | |
| 5,681,311 A | 10/1997 | Foley et al. | 606/61 |
| 5,681,319 A | 10/1997 | Biedermann et al. | 606/104 |
| 5,683,391 A | 11/1997 | Boyd | 606/61 |
| 5,683,392 A | 11/1997 | Richelsoph et al. | 606/61 |
| 5,683,393 A | 11/1997 | Ralph | 606/61 |
| 5,688,272 A | 11/1997 | Montague et al. | 606/61 |
| 5,688,273 A | 11/1997 | Errico et al. | 606/61 |
| 5,690,629 A | 11/1997 | Asher et al. | 606/61 |
| 5,690,632 A | 11/1997 | Schwartz et al. | 606/73 |
| 5,690,633 A | 11/1997 | Taylor et al. | 606/73 |
| 5,693,053 A | 12/1997 | Estes | 606/61 |
| 5,697,929 A | 12/1997 | Mellinger | 606/61 |
| 5,700,292 A | 12/1997 | Margulies | 623/17 |
| 5,702,392 A | 12/1997 | Wu et al. | 606/61 |
| 5,702,394 A | 12/1997 | Henry et al. | 606/61 |
| 5,702,395 A | 12/1997 | Hopf | 606/61 |
| 5,702,396 A | 12/1997 | Hoenig et al. | 606/69 |
| 5,702,399 A | 12/1997 | Kilpela et al. | 606/72 |
| 5,702,452 A | 12/1997 | Argenson et al. | 623/17 |
| 5,713,900 A | 2/1998 | Benzel et al. | 606/61 |
| 5,713,904 A | 2/1998 | Errico et al. | 606/73 |
| 5,716,355 A | 2/1998 | Jackson et al. | 606/61 |
| 5,716,356 A | 2/1998 | Biedermann et al. | 606/61 |
| 5,716,357 A | 2/1998 | Rogozinski | 606/61 |
| 5,716,358 A | 2/1998 | Ochoa et al. | 606/62 |
| 5,716,359 A | 2/1998 | Ojima et al. | 606/76 |
| 5,720,751 A | 2/1998 | Jackson | 606/86 |
| 5,725,528 A | 3/1998 | Errico et al. | 606/61 |
| 5,725,582 A | 3/1998 | Bevan et al. | 623/17 |
| 5,728,098 A | 3/1998 | Sherman et al. | 606/61 |
| 5,733,286 A | 3/1998 | Errico et al. | 606/61 |
| 5,735,851 A | 4/1998 | Errico et al. | 606/61 |
| 5,741,254 A | 4/1998 | Henry et al. | 606/61 |
| 5,743,907 A | 4/1998 | Asher et al. | 606/61 |
| 5,743,911 A | 4/1998 | Cotrel | 606/61 |
| 5,752,957 A | 5/1998 | Ralph et al. | 606/61 |
| 5,766,254 A | 6/1998 | Gelbard | 623/17 |
| 5,776,135 A | 7/1998 | Errico et al. | |
| 5,782,833 A | 7/1998 | Haider | 606/61 |
| 5,785,711 A | 7/1998 | Errico et al. | 606/61 |
| 5,797,911 A | 8/1998 | Sherman et al. | 606/61 |

| | | | | | | |
|---|---|---|---|---|---|---|
| 5,800,435 A | 9/1998 | Errico et al. ............... 606/61 | | 6,458,132 B2 | 10/2002 | Choi ............... 606/61 |
| 5,810,819 A | 9/1998 | Errico et al. ............... 606/61 | | 6,468,276 B1 | 10/2002 | McKay ............... 606/61 |
| 5,863,293 A | 1/1999 | Richelsoph ............... 606/61 | | 6,471,705 B1 | 10/2002 | Biedermann et al. ........... 606/61 |
| 5,868,745 A | 2/1999 | Alleyne | | 6,475,219 B1 | 11/2002 | Shelokov |
| 5,879,350 A | 3/1999 | Sherman et al. ............... 606/61 | | 6,478,797 B1 | 11/2002 | Paul ............... 606/61 |
| 5,885,286 A | 3/1999 | Sherman et al. ............... 606/61 | | 6,482,207 B1 | 11/2002 | Errico ............... 606/61 |
| 5,891,145 A | 4/1999 | Morrison et al. ............... 606/61 | | 6,485,491 B1 | 11/2002 | Farris et al. ............... 606/61 |
| 5,899,904 A | 5/1999 | Errico et al. ............... 606/61 | | 6,488,681 B2 | 12/2002 | Martin et al. ............... 606/61 |
| RE36,221 E | 6/1999 | Breard et al. ............... 606/61 | | 6,520,962 B1 | 2/2003 | Taylor et al. ............... 606/61 |
| 5,910,142 A | 6/1999 | Tatar ............... 606/61 | | 6,520,990 B1 | 2/2003 | Ray ............... 623/17.11 |
| 5,925,047 A | 7/1999 | Errico et al. ............... 606/65 | | 6,537,276 B2 | 3/2003 | Metz-Stavenhagen ......... 606/61 |
| 5,928,231 A | 7/1999 | Klein et al. ............... 606/60 | | 6,540,748 B2 | 4/2003 | Lombardo ............... 606/61 |
| 5,928,232 A | 7/1999 | Howland et al. ............... 606/61 | | 6,540,749 B2 | 4/2003 | Schäfer et al. ............... 606/61 |
| 5,928,233 A | 7/1999 | Apfelbaum et al. ............... 606/61 | | 6,547,789 B1 | 4/2003 | Ventre et al. ............... 606/61 |
| 5,947,965 A | 9/1999 | Bryan ............... 606/61 | | 6,554,831 B1 | 4/2003 | Rivard et al. |
| 5,947,969 A | 9/1999 | Errico et al. ............... 606/61 | | 6,554,832 B2 | 4/2003 | Shluzas ............... 606/61 |
| 5,954,725 A | 9/1999 | Sherman et al. ............... 606/78 | | 6,554,834 B1 | 4/2003 | Crozet et al. ............... 606/65 |
| 5,961,517 A | 10/1999 | Biedermann et al. ........... 606/61 | | 6,565,565 B1 | 5/2003 | Yuan et al. ............... 606/61 |
| 5,964,760 A | 10/1999 | Richelsoph ............... 606/61 | | 6,565,566 B1 | 5/2003 | Wagner et al. ............... 606/61 |
| 5,980,521 A | 11/1999 | Montague et al. ............... 606/61 | | 6,565,567 B1 | 5/2003 | Haider ............... 606/61 |
| 5,980,523 A | 11/1999 | Jackson ............... 606/61 | | 6,565,605 B2 | 5/2003 | Goble et al. ............... 623/17.11 |
| 5,984,922 A | 11/1999 | McKay ............... 606/61 | | 6,572,617 B1 | 6/2003 | Senegas ............... 606/61 |
| 5,989,251 A | 11/1999 | Nichols ............... 606/61 | | 6,572,653 B1 | 6/2003 | Simonson ............... 623/17.13 |
| 5,989,254 A | 11/1999 | Katz ............... 606/73 | | 6,579,290 B1 | 6/2003 | Hardcastle et al. ............ 606/61 |
| 6,001,098 A | 12/1999 | Metz-Stavenhagen et al. 606/61 | | 6,585,737 B1 | 7/2003 | Baccelli et al. ............... 606/61 |
| 6,004,322 A | 12/1999 | Bernstein ............... 606/61 | | 6,589,243 B1 | 7/2003 | Viart et al. |
| 6,010,503 A | 1/2000 | Richelsoph et al. ............ 606/61 | | 6,616,669 B2 | 9/2003 | Ogilvie et al. ............... 606/61 |
| 6,015,409 A | 1/2000 | Jackson ............... 606/61 | | 6,623,485 B2 | 9/2003 | Doubler et al. ............... 606/61 |
| 6,033,410 A | 3/2000 | McLean et al. | | 6,626,905 B1 | 9/2003 | Schmiel et al. ............... 606/61 |
| 6,036,693 A | 3/2000 | Yuan et al. ............... 606/61 | | 6,626,908 B2 | 9/2003 | Cooper et al. ............... 606/61 |
| 6,050,997 A * | 4/2000 | Mullane ............... 606/250 | | 6,645,207 B2 | 11/2003 | Dixon et al. ............... 606/61 |
| 6,053,917 A | 4/2000 | Sherman et al. ............... 606/61 | | 6,652,526 B1 | 11/2003 | Arafiles ............... 606/61 |
| 6,063,089 A | 5/2000 | Errico et al. ............... 606/61 | | 6,656,181 B2 | 12/2003 | Dixon et al. ............... 606/69 |
| 6,077,262 A | 6/2000 | Schläpfer et al. ............... 606/61 | | 6,660,004 B2 | 12/2003 | Barker et al. ............... 606/61 |
| 6,086,588 A | 7/2000 | Ameil et al. ............... 606/61 | | 6,660,005 B2 | 12/2003 | Toyama et al. ............... 606/61 |
| 6,090,111 A | 7/2000 | Nichols ............... 606/61 | | 6,676,661 B1 | 1/2004 | Martin Benlloch et al. |
| 6,096,039 A | 8/2000 | Stoltenberg et al. ............ 606/61 | | 6,695,845 B2 | 2/2004 | Dixon et al. ............... 606/70 |
| 6,113,600 A | 9/2000 | Drummond et al. ............ 606/61 | | 6,706,045 B2 | 3/2004 | Lin et al. ............... 606/61 |
| 6,113,601 A | 9/2000 | Tatar ............... 606/61 | | 6,709,434 B1 | 3/2004 | Gournay et al. ............... 606/61 |
| 6,123,706 A | 9/2000 | Lange | | 6,716,213 B2 | 4/2004 | Shitoto ............... 606/61 |
| 6,127,597 A | 10/2000 | Beyar et al. ............... 623/16 | | 6,716,214 B1 | 4/2004 | Jackson ............... 606/61 |
| 6,132,430 A | 10/2000 | Wagner ............... 606/61 | | 6,726,689 B2 | 4/2004 | Jackson ............... 606/73 |
| 6,132,434 A | 10/2000 | Sherman et al. ............... 606/78 | | 6,736,820 B2 | 5/2004 | Biedermann et al. ........... 606/73 |
| 6,132,464 A | 10/2000 | Martin | | 6,740,086 B2 | 5/2004 | Richelsoph |
| 6,136,000 A | 10/2000 | Louis et al. ............... 606/61 | | 6,749,614 B2 | 6/2004 | Teitelbaum et al. ............ 606/61 |
| 6,146,383 A | 11/2000 | Studer et al. ............... 606/61 | | 6,752,807 B2 | 6/2004 | Lin et al. ............... 606/61 |
| 6,171,311 B1 | 1/2001 | Richelsoph ............... 606/61 | | 6,755,829 B1 | 6/2004 | Bono et al. ............... 606/61 |
| 6,193,720 B1 | 2/2001 | Yuan et al. ............... 606/61 | | 6,755,835 B2 | 6/2004 | Schultheiss et al. ............ 606/73 |
| 6,197,028 B1 | 3/2001 | Ray et al. ............... 606/61 | | 6,761,719 B2 | 7/2004 | Justis et al. ............... 606/61 |
| 6,210,413 B1 | 4/2001 | Justis et al. ............... 606/61 | | 6,783,526 B1 | 8/2004 | Lin et al. ............... 606/61 |
| 6,217,578 B1 | 4/2001 | Crozet et al. ............... 606/61 | | 6,783,527 B2 | 8/2004 | Drewry et al. ............... 606/61 |
| 6,248,106 B1 | 6/2001 | Ferree ............... 606/61 | | 6,786,907 B2 | 9/2004 | Lange ............... 606/61 |
| 6,254,602 B1 | 7/2001 | Justis ............... 606/61 | | 6,793,656 B1 | 9/2004 | Mathews ............... 606/61 |
| 6,261,287 B1 | 7/2001 | Metz-Stavenhagen ......... 606/61 | | 6,805,695 B2 | 10/2004 | Keith et al. ............... 606/61 |
| 6,267,765 B1 | 7/2001 | Taylor et al. | | 6,805,714 B2 | 10/2004 | Sutcliffe ............... 623/17.11 |
| 6,273,888 B1 | 8/2001 | Justis ............... 606/61 | | 6,811,567 B2 | 11/2004 | Reiley ............... 623/17.11 |
| 6,273,914 B1 | 8/2001 | Papas ............... 623/17.11 | | 6,827,743 B2 | 12/2004 | Eisermann et al. |
| 6,280,442 B1 | 8/2001 | Barker et al. | | 6,832,999 B2 | 12/2004 | Ueyama et al. ............... 606/61 |
| 6,280,443 B1 | 8/2001 | Gu et al. ............... 606/61 | | 6,840,940 B2 | 1/2005 | Ralph et al. ............... 606/61 |
| 6,287,311 B1 | 9/2001 | Sherman et al. ............... 606/78 | | 6,843,791 B2 | 1/2005 | Serhan ............... 606/61 |
| 6,293,949 B1 | 9/2001 | Justis et al. ............... 606/61 | | 6,852,128 B2 | 2/2005 | Lange ............... 623/17.11 |
| 6,302,882 B1 | 10/2001 | Lin et al. | | 6,858,029 B2 | 2/2005 | Yeh |
| 6,302,888 B1 | 10/2001 | Mellinger et al. ............... 606/73 | | 6,858,030 B2 | 2/2005 | Martin et al. ............... 606/61 |
| 6,309,391 B1 | 10/2001 | Crandall et al. ............... 606/61 | | 6,869,433 B2 | 3/2005 | Glascott ............... 606/73 |
| 6,325,802 B1 | 12/2001 | Frigg ............... 606/61 | | 6,875,211 B2 | 4/2005 | Nichols et al. ............... 606/61 |
| 6,328,740 B1 | 12/2001 | Richelsoph ............... 606/61 | | 6,881,215 B2 | 4/2005 | Assaker et al. ............... 606/61 |
| 6,344,057 B1 | 2/2002 | Rabbe et al. ............... 623/17 | | 6,883,520 B2 | 4/2005 | Lambrecht ............... 128/898 |
| 6,355,040 B1 | 3/2002 | Richelsoph et al. ............ 606/61 | | 6,887,242 B2 * | 5/2005 | Doubler et al. ............... 606/274 |
| 6,379,354 B1 | 4/2002 | Rogozinski ............... 606/61 | | 6,899,714 B2 | 5/2005 | Vaughan ............... 606/61 |
| 6,402,749 B1 | 6/2002 | Ashman ............... 606/61 | | 6,918,911 B2 | 7/2005 | Biedermann et al. ........... 606/61 |
| 6,402,751 B1 | 6/2002 | Hoeck et al. ............... 606/61 | | 6,932,817 B2 | 8/2005 | Baynham et al. ............... 606/61 |
| 6,402,752 B2 | 6/2002 | Schäffler-Wachter et al. . 606/61 | | 6,945,974 B2 | 9/2005 | Dalton ............... 606/70 |
| 6,413,257 B1 | 7/2002 | Lin et al. ............... 606/61 | | 6,951,561 B2 | 10/2005 | Warren et al. ............... 606/73 |
| 6,416,515 B1 | 7/2002 | Wagner ............... 606/61 | | 6,964,666 B2 | 11/2005 | Jackson ............... 606/61 |
| 6,423,064 B1 | 7/2002 | Kluger ............... 606/61 | | 6,966,910 B2 | 11/2005 | Ritland ............... 606/61 |
| 6,440,169 B1 | 8/2002 | Elberg et al. ............... 623/17.16 | | 6,986,771 B2 | 1/2006 | Paul et al. ............... 606/61 |
| 6,451,021 B1 | 9/2002 | Ralph et al. ............... 606/61 | | 6,991,632 B2 | 1/2006 | Ritland ............... 606/61 |
| 6,454,773 B1 | 9/2002 | Sherman et al. ............... 606/78 | | 7,008,423 B2 | 3/2006 | Assaker et al. ............... 606/61 |
| 6,458,131 B1 | 10/2002 | Ray ............... 606/61 | | 7,011,685 B2 | 3/2006 | Arnin et al. ............... 623/17.16 |

| Patent No. | Date | Name | Class |
|---|---|---|---|
| 7,018,378 B2 | 3/2006 | Biedermann et al. | 606/61 |
| 7,018,379 B2 | 3/2006 | Drewry | 606/61 |
| 7,022,122 B2 | 4/2006 | Amrein et al. | 606/61 |
| 7,029,475 B2 | 4/2006 | Panjabi | 606/61 |
| 7,033,392 B2 | 4/2006 | Schmiel | |
| 7,048,736 B2 | 5/2006 | Robinson et al. | 606/61 |
| 7,051,451 B2 | 5/2006 | Augostino et al. | 33/512 |
| 7,060,066 B2 | 6/2006 | Zhao et al. | 606/61 |
| 7,074,237 B2 | 7/2006 | Goble et al. | 623/17.11 |
| 7,081,117 B2 | 7/2006 | Bono et al. | 606/61 |
| 7,083,621 B2 | 8/2006 | Shaolian et al. | 606/61 |
| 7,083,622 B2 | 8/2006 | Simonson | 606/61 |
| 7,087,056 B2 | 8/2006 | Vaughan | 606/61 |
| 7,087,057 B2 | 8/2006 | Konieczynski et al. | 606/73 |
| 7,087,084 B2 | 8/2006 | Reiley | 623/17.11 |
| 7,090,698 B2 | 8/2006 | Goble et al. | 623/17.11 |
| 7,101,398 B2 | 9/2006 | Dooris et al. | 623/13.11 |
| 7,104,991 B2 | 9/2006 | Dixon | |
| 7,104,992 B2 | 9/2006 | Bailey | 606/61 |
| 7,107,091 B2 | 9/2006 | Jutras et al. | 600/429 |
| 7,125,410 B2 | 10/2006 | Freudiger | 606/61 |
| 7,125,426 B2 | 10/2006 | Moumene et al. | 623/23.42 |
| 7,137,985 B2 | 11/2006 | Jahng | |
| 7,163,538 B2 * | 1/2007 | Altarac et al. | 606/86 A |
| 7,189,235 B2 | 3/2007 | Cauthen | |
| 7,214,227 B2 | 5/2007 | Colleran et al. | 606/61 |
| 7,250,052 B2 | 7/2007 | Landry et al. | 606/61 |
| 7,270,665 B2 | 9/2007 | Morrison et al. | |
| 7,282,064 B2 | 10/2007 | Chin | 623/17.15 |
| 7,294,128 B2 | 11/2007 | Alleyne et al. | |
| 7,294,129 B2 | 11/2007 | Hawkins et al. | 606/61 |
| 7,306,603 B2 | 12/2007 | Boehm, Jr. et al. | 606/61 |
| 7,306,606 B2 | 12/2007 | Sasing | 606/61 |
| 7,309,355 B2 | 12/2007 | Donnelly et al. | |
| 7,326,210 B2 | 2/2008 | Jahng et al. | 606/61 |
| 7,335,201 B2 * | 2/2008 | Doubler et al. | 606/264 |
| 7,338,490 B2 | 3/2008 | Ogilvie et al. | |
| 7,338,491 B2 | 3/2008 | Baker et al. | |
| 7,344,539 B2 | 3/2008 | Serhan et al. | |
| 7,361,196 B2 | 4/2008 | Fallin et al. | |
| 7,377,923 B2 | 5/2008 | Purcell et al. | |
| 7,445,627 B2 | 11/2008 | Hawkes et al. | |
| 7,455,684 B2 | 11/2008 | Gradel et al. | |
| 7,476,238 B2 | 1/2009 | Panjabi | |
| 7,479,156 B2 | 1/2009 | Lourdel et al. | |
| 7,481,828 B2 | 1/2009 | Mazda et al. | |
| 7,491,218 B2 | 2/2009 | Landry et al. | |
| 7,503,924 B2 | 3/2009 | Lee et al. | |
| 7,513,905 B2 | 4/2009 | Jackson | |
| 7,513,911 B2 | 4/2009 | Lambrecht et al. | |
| 7,520,879 B2 | 4/2009 | Justis | |
| 7,530,992 B2 | 5/2009 | Biedermann et al. | |
| 7,533,672 B2 | 5/2009 | Morgan et al. | |
| 7,553,320 B2 | 6/2009 | Molz, IV et al. | |
| 7,553,329 B2 | 6/2009 | Lambrecht et al. | |
| 7,559,943 B2 | 7/2009 | Mujwid | |
| 7,563,274 B2 | 7/2009 | Justis et al. | |
| 7,572,279 B2 | 8/2009 | Jackson | |
| 7,578,833 B2 | 8/2009 | Bray | |
| 7,585,312 B2 | 9/2009 | Rawlins et al. | |
| 7,588,575 B2 | 9/2009 | Colleran et al. | |
| 7,588,588 B2 | 9/2009 | Spitler et al. | |
| 7,594,924 B2 | 9/2009 | Albert et al. | |
| 7,597,707 B2 | 10/2009 | Freudiger | |
| 7,601,166 B2 | 10/2009 | Biedermann et al. | |
| 7,608,095 B2 | 10/2009 | Yuan et al. | |
| 7,611,526 B2 | 11/2009 | Carl et al. | |
| 7,615,068 B2 | 11/2009 | Timm et al. | |
| 7,625,394 B2 | 12/2009 | Molz, IV et al. | |
| 7,625,396 B2 | 12/2009 | Jackson | |
| 7,635,379 B2 | 12/2009 | Callahan et al. | |
| 7,648,520 B2 | 1/2010 | Markworth | |
| 7,648,522 B2 | 1/2010 | David | |
| 7,662,172 B2 | 2/2010 | Warnick | |
| 7,662,173 B2 | 2/2010 | Cragg et al. | |
| 7,662,175 B2 | 2/2010 | Jackson | |
| 7,674,293 B2 | 3/2010 | Kuiper et al. | |
| 7,678,136 B2 | 3/2010 | Doubler et al. | |
| 7,678,137 B2 | 3/2010 | Butler et al. | |
| 7,682,377 B2 | 3/2010 | Konieczynski et al. | |
| 7,691,129 B2 | 4/2010 | Felix | |
| 7,691,132 B2 | 4/2010 | Landry et al. | |
| 7,699,873 B2 | 4/2010 | Stevenson et al. | |
| 7,699,875 B2 | 4/2010 | Timm et al. | |
| 7,704,270 B2 | 4/2010 | De Coninck | |
| 7,708,762 B2 | 5/2010 | McCarthy et al. | |
| 7,713,287 B2 | 5/2010 | Timm et al. | |
| 7,713,288 B2 | 5/2010 | Timm et al. | |
| 7,717,939 B2 | 5/2010 | Ludwig et al. | |
| 7,722,646 B2 | 5/2010 | Ralph et al. | |
| 7,722,649 B2 | 5/2010 | Biedermann et al. | |
| 7,722,654 B2 | 5/2010 | Taylor et al. | |
| 7,727,259 B2 | 6/2010 | Park | |
| 7,727,261 B2 | 6/2010 | Barker et al. | |
| 7,731,734 B2 * | 6/2010 | Clement et al. | 606/246 |
| 7,731,736 B2 | 6/2010 | Guenther et al. | |
| 7,763,051 B2 | 7/2010 | Labrom et al. | |
| 7,763,052 B2 | 7/2010 | Jahng | |
| 7,766,944 B2 | 8/2010 | Metz-Stavenhagen | |
| 7,766,945 B2 | 8/2010 | Nilsson et al. | |
| 7,776,071 B2 | 8/2010 | Fortin et al. | |
| 7,785,350 B2 | 8/2010 | Eckhardt et al. | |
| 7,785,354 B2 | 8/2010 | Biedermann et al. | |
| 7,789,896 B2 | 9/2010 | Jackson | |
| 7,794,477 B2 | 9/2010 | Melkent et al. | |
| 7,794,481 B2 | 9/2010 | Molz, IV et al. | |
| 7,799,060 B2 | 9/2010 | Lange et al. | |
| 7,803,189 B2 | 9/2010 | Koske | |
| 7,806,913 B2 | 10/2010 | Fanger et al. | |
| 7,806,914 B2 | 10/2010 | Boyd et al. | |
| 7,811,288 B2 | 10/2010 | Jones et al. | |
| 7,811,309 B2 | 10/2010 | Timm et al. | |
| 7,811,311 B2 | 10/2010 | Markworth et al. | |
| 7,815,664 B2 | 10/2010 | Sherman et al. | |
| 7,815,665 B2 | 10/2010 | Jahng et al. | |
| 7,819,899 B2 | 10/2010 | Lancial | |
| 7,819,901 B2 | 10/2010 | Yuan et al. | |
| 7,819,902 B2 | 10/2010 | Abdelgany et al. | |
| 7,828,824 B2 | 11/2010 | Kwak et al. | |
| 7,828,825 B2 | 11/2010 | Bruneau et al. | |
| 7,828,826 B2 | 11/2010 | Drewry et al. | |
| 7,828,830 B2 | 11/2010 | Thramann et al. | |
| 7,833,250 B2 | 11/2010 | Jackson | |
| 7,833,256 B2 | 11/2010 | Biedermann et al. | |
| 7,842,072 B2 | 11/2010 | Dawson | |
| 7,850,715 B2 | 12/2010 | Bonouskou et al. | |
| 7,850,718 B2 * | 12/2010 | Bette et al. | 606/267 |
| 7,854,752 B2 | 12/2010 | Colleran et al. | |
| 7,857,833 B2 | 12/2010 | Abdou | |
| 7,857,834 B2 | 12/2010 | Boschert | |
| 7,862,586 B2 | 1/2011 | Malek | |
| 7,862,587 B2 | 1/2011 | Jackson | |
| 7,862,588 B2 | 1/2011 | Abdou | |
| 7,862,591 B2 | 1/2011 | Dewey et al. | |
| 7,862,594 B2 | 1/2011 | Abdelgany et al. | |
| 7,871,413 B2 | 1/2011 | Park et al. | |
| 7,875,059 B2 | 1/2011 | Patterson et al. | |
| 7,875,060 B2 | 1/2011 | Chin | |
| 7,879,074 B2 | 2/2011 | Kwak et al. | |
| 7,892,266 B2 | 2/2011 | Carli | |
| 7,909,856 B2 | 3/2011 | Yuan et al. | |
| 7,914,558 B2 | 3/2011 | Landry et al. | |
| 7,918,792 B2 | 4/2011 | Drzyzga et al. | |
| 7,927,359 B2 | 4/2011 | Trautwein | |
| 2003/0004511 A1 | 1/2003 | Ferree | |
| 2003/0171749 A1 | 9/2003 | Le Couedic et al. | |
| 2004/0015166 A1 | 1/2004 | Gorek | |
| 2004/0034374 A1 | 2/2004 | Zatzsch et al. | |
| 2004/0049285 A1 | 3/2004 | Haas | |
| 2004/0097925 A1 | 5/2004 | Boehm, Jr. et al. | |
| 2004/0111088 A1 | 6/2004 | Picetti et al. | |
| 2004/0122425 A1 | 6/2004 | Suzuki et al. | |
| 2004/0147928 A1 | 7/2004 | Landry et al. | |
| 2004/0153077 A1 | 8/2004 | Biedermann et al. | |
| 2004/0158247 A1 | 8/2004 | Sitiso et al. | |
| 2004/0162560 A1 | 8/2004 | Raynor et al. | |
| 2004/0172022 A1 | 9/2004 | Landry et al. | |
| 2004/0172024 A1 | 9/2004 | Gorek | |

| | | | |
|---|---|---|---|
| 2004/0215192 | A1 | 10/2004 | Justis et al. |
| 2004/0225289 | A1 | 11/2004 | Biedermann et al. |
| 2004/0230192 | A1 | 11/2004 | Graf |
| 2004/0230304 | A1 | 11/2004 | Yuan et al. |
| 2005/0049589 | A1 | 3/2005 | Jackson |
| 2005/0080415 | A1 | 4/2005 | Keyer et al. |
| 2005/0090822 | A1 | 4/2005 | DiPoto |
| 2005/0096652 | A1 | 5/2005 | Burton |
| 2005/0107788 | A1 | 5/2005 | Beaurain et al. |
| 2005/0113923 | A1 | 5/2005 | Acker et al. |
| 2005/0131404 | A1 | 6/2005 | Mazda et al. |
| 2005/0131406 | A1 | 6/2005 | Reiley et al. |
| 2005/0143737 | A1 | 6/2005 | Pafford et al. |
| 2005/0171537 | A1 | 8/2005 | Mazel et al. |
| 2005/0171543 | A1 | 8/2005 | Timm et al. |
| 2005/0177156 | A1 | 8/2005 | Timm et al. |
| 2005/0177157 | A1 | 8/2005 | Jahng |
| 2005/0177164 | A1 | 8/2005 | Walters et al. |
| 2005/0182400 | A1 | 8/2005 | White |
| 2005/0182401 | A1 | 8/2005 | Timm et al. |
| 2005/0192569 | A1 | 9/2005 | Nichols et al. |
| 2005/0228382 | A1 | 10/2005 | Richelsoph et al. |
| 2005/0228385 | A1 | 10/2005 | Iott et al. |
| 2005/0240180 | A1 | 10/2005 | Vienney et al. |
| 2005/0240265 | A1 | 10/2005 | Kuiper et al. |
| 2005/0261770 | A1 | 11/2005 | Kuiper et al. |
| 2005/0267470 | A1 | 12/2005 | McBride |
| 2005/0277922 | A1 | 12/2005 | Trieu et al. |
| 2005/0288670 | A1 | 12/2005 | Panjabi et al. |
| 2006/0025771 | A1 | 2/2006 | Jackson |
| 2006/0036324 | A1 | 2/2006 | Sachs et al. |
| 2006/0052783 | A1 | 3/2006 | Dant et al. |
| 2006/0052784 | A1 | 3/2006 | Dant et al. |
| 2006/0052786 | A1 | 3/2006 | Dant et al. |
| 2006/0058787 | A1 | 3/2006 | David |
| 2006/0058788 | A1 | 3/2006 | Hammer et al. |
| 2006/0079894 | A1 | 4/2006 | Colleran et al. |
| 2006/0079896 | A1 | 4/2006 | Kwak et al. |
| 2006/0084978 | A1 | 4/2006 | Mokhtar |
| 2006/0084982 | A1 | 4/2006 | Kim |
| 2006/0084983 | A1 | 4/2006 | Kim |
| 2006/0084984 | A1 | 4/2006 | Kim |
| 2006/0084985 | A1 | 4/2006 | Kim |
| 2006/0084987 | A1 | 4/2006 | Kim |
| 2006/0084988 | A1 | 4/2006 | Kim |
| 2006/0084989 | A1 | 4/2006 | Dickinson et al. |
| 2006/0084990 | A1 | 4/2006 | Gournay et al. |
| 2006/0085069 | A1 | 4/2006 | Kim |
| 2006/0085070 | A1 | 4/2006 | Kim |
| 2006/0089643 | A1 | 4/2006 | Mujwid |
| 2006/0095035 | A1 | 5/2006 | Jones et al. |
| 2006/0106383 | A1 | 5/2006 | Biedermann et al. |
| 2006/0111712 | A1 | 5/2006 | Jackson |
| 2006/0122620 | A1 | 6/2006 | Kim |
| 2006/0129148 | A1 | 6/2006 | Simmons et al. |
| 2006/0129149 | A1 | 6/2006 | Iott et al. |
| 2006/0142761 | A1 | 6/2006 | Landry et al. |
| 2006/0149242 | A1 | 7/2006 | Kraus et al. |
| 2006/0149244 | A1 | 7/2006 | Amrein et al. |
| 2006/0149380 | A1 | 7/2006 | Lotz et al. |
| 2006/0161153 | A1 | 7/2006 | Hawkes et al. |
| 2006/0195093 | A1 | 8/2006 | Jahng |
| 2006/0200128 | A1 | 9/2006 | Mueller |
| 2006/0200131 | A1 | 9/2006 | Chao et al. |
| 2006/0229607 | A1 | 10/2006 | Brumfield |
| 2006/0229613 | A1 | 10/2006 | Timm et al. |
| 2006/0235385 | A1 | 10/2006 | Whipple |
| 2006/0235389 | A1 | 10/2006 | Albert et al. |
| 2006/0235392 | A1 | 10/2006 | Hammer et al. |
| 2006/0235393 | A1 | 10/2006 | Bono et al. |
| 2006/0241600 | A1 | 10/2006 | Ensign et al. |
| 2006/0241601 | A1 | 10/2006 | Trautwein et al. |
| 2006/0241603 | A1 | 10/2006 | Jackson |
| 2006/0241757 | A1 | 10/2006 | Anderson |
| 2006/0247623 | A1 | 11/2006 | Anderson et al. |
| 2006/0247631 | A1 | 11/2006 | Ahn et al. |
| 2006/0247637 | A1 | 11/2006 | Colleran et al. |
| 2006/0253118 | A1 | 11/2006 | Bailey |
| 2006/0264935 | A1 | 11/2006 | White |
| 2006/0264937 | A1 | 11/2006 | White |
| 2006/0276897 | A1 | 12/2006 | Winslow et al. |
| 2006/0282073 | A1 | 12/2006 | Simanovsky |
| 2006/0282078 | A1 | 12/2006 | Labrom et al. |
| 2007/0016190 | A1 | 1/2007 | Martinez et al. |
| 2007/0016194 | A1 | 1/2007 | Shaolian et al. |
| 2007/0016201 | A1 | 1/2007 | Freudiger |
| 2007/0049936 | A1 | 3/2007 | Colleran et al. |
| 2007/0083200 | A1 | 4/2007 | Gittings et al. |
| 2007/0088359 | A1 | 4/2007 | Woods et al. |
| 2007/0093814 | A1 | 4/2007 | Callahan, II et al. |
| 2007/0093820 | A1 | 4/2007 | Freudiger |
| 2007/0093821 | A1 | 4/2007 | Freudiger |
| 2007/0118122 | A1 | 5/2007 | Butler et al. |
| 2007/0123871 | A1 | 5/2007 | Jahng |
| 2007/0161994 | A1 | 7/2007 | Lowery et al. |
| 2007/0162007 | A1 | 7/2007 | Shoham |
| 2007/0167946 | A1 | 7/2007 | Triplett et al. |
| 2007/0167947 | A1 | 7/2007 | Gittings |
| 2007/0198014 | A1 | 8/2007 | Graf et al. |
| 2007/0213719 | A1 | 9/2007 | Hudgins et al. |
| 2007/0233068 | A1 | 10/2007 | Bruneau et al. |
| 2007/0233072 | A1 | 10/2007 | Dickinson et al. |
| 2007/0233090 | A1 | 10/2007 | Naifeh et al. |
| 2007/0233091 | A1 | 10/2007 | Naifeh et al. |
| 2007/0233092 | A1 | 10/2007 | Falahee |
| 2007/0233093 | A1 | 10/2007 | Falahee |
| 2007/0233094 | A1 | 10/2007 | Colleran et al. |
| 2007/0250061 | A1 | 10/2007 | Chin et al. |
| 2007/0270836 | A1 | 11/2007 | Bruneau et al. |
| 2007/0270838 | A1 | 11/2007 | Bruneau et al. |
| 2007/0276380 | A1 | 11/2007 | Jahng et al. |
| 2007/0288009 | A1 | 12/2007 | Brown et al. |
| 2007/0288012 | A1 | 12/2007 | Colleran et al. |
| 2008/0009864 | A1 | 1/2008 | Forton et al. |
| 2008/0021459 | A1 | 1/2008 | Lim |
| 2008/0021461 | A1 | 1/2008 | Barker et al. |
| 2008/0033433 | A1 | 2/2008 | Implicito |
| 2008/0039838 | A1 | 2/2008 | Landry et al. |
| 2008/0051787 | A1 | 2/2008 | Remington et al. |
| 2008/0065073 | A1 | 3/2008 | Perriello et al. |
| 2008/0065075 | A1 | 3/2008 | Dant et al. |
| 2008/0065079 | A1 | 3/2008 | Bruneau et al. |
| 2008/0071273 | A1 | 3/2008 | Hawkes et al. |
| 2008/0077139 | A1 | 3/2008 | Landry et al. |
| 2008/0183215 | A1 | 7/2008 | Altarac et al. |
| 2008/0195208 | A1 | 8/2008 | Castellvi et al. |
| 2008/0262554 | A1 | 10/2008 | Hayes et al. |
| 2008/0312693 | A1 | 12/2008 | Trautwein et al. |
| 2010/0174317 | A1 | 7/2010 | Timm et al. |
| 2010/0198270 | A1 | 8/2010 | Barker et al. |
| 2010/0222819 | A1 | 9/2010 | Timm et al. |

FOREIGN PATENT DOCUMENTS

| | | | |
|---|---|---|---|
| DE | 3639810 | A1 | 5/1988 |
| EP | 0128058 | B1 | 4/1988 |
| EP | 0669109 | B1 | 8/1995 |
| EP | 0982007 | | 3/2000 |
| EP | 1281362 | A2 | 2/2003 |
| EP | 1330987 | A1 | 7/2003 |
| FR | 2612070 | A1 | 9/1988 |
| FR | 2615095 | A1 | 11/1988 |
| FR | 2844180 | A1 | 3/2004 |
| FR | 2880256 | B1 | 7/2006 |
| GB | 780652 | | 8/1957 |
| GB | 2173104 | | 10/1986 |
| GB | 2382304 | | 5/2003 |
| KR | 20080072848 | | 8/2008 |
| WO | WO 87/07134 | | 12/1987 |
| WO | WO 94/21185 | | 9/1994 |
| WO | WO 98/27884 | | 7/1998 |
| WO | WO 01/45576 | | 6/2001 |
| WO | WO 01/91656 | | 12/2001 |
| WO | WO 02/07621 | | 1/2002 |
| WO | WO 02/07622 | | 1/2002 |
| WO | WO 02/17803 | | 3/2002 |
| WO | WO 02/39921 | | 5/2002 |
| WO | WO 02/43603 | | 6/2002 |
| WO | WO 02/102259 | | 12/2002 |

| | | |
|---|---|---|
| WO | WO 03/007828 | 1/2003 |
| WO | WO 03/009737 | 2/2003 |
| WO | WO 03/015647 | 2/2003 |
| WO | WO 03/037216 | 5/2003 |
| WO | WO 03/077806 | 9/2003 |
| WO | WO2004/024011 | 3/2004 |
| WO | WO2004/034916 | 4/2004 |
| WO | WO2006/033503 | 3/2006 |
| WO | WO2006/066685 | 6/2006 |
| WO | WO2006/105935 | 10/2006 |
| WO | WO2007064324 | 6/2007 |
| WO | WO2007/080317 | 7/2007 |
| WO | WO2008/034130 | 3/2008 |
| WO | WO2008/073544 | 6/2008 |

OTHER PUBLICATIONS

Zimmer, Inc. Website, 2007; Zimmer Spine, product description for Dynesis—The Dynamic Stabilization System, 5 pages, <http://www.zimmer.com/ctl?template=IN&action=1&op=global&id=9165&pr=Y>.

Ito Medical Instrument website, 2006; ITOIKA Medical Instruments, product description for S-Plate, 15 pages, <http://ito-ika.co.jp/s-plate/splate1.pdf and http://ito-ika.co.jp/s-plate/splate1.pdf>.

"Flexible rods and the case for dynamic stabilization," Jason M. Highsmith, M.D., et al., Neurosurg. Focus, vol. 22, Jan. 2007, pp. 1-5.

"The Spinous Process: The Forgotten Appendage," Kenneth R. Kattan, M. D. eta l., Skeletal Radiology, vol. 6, 1981, pp. 199-204.

"Morphological and functional changes of the lumbar spinous processes in the elderly," R. Scapinelli, Surgical Radiologic Anatomy, vol. 11, 1989, pp. 129-133.

"The Paraspinal Sacrospinalis-Splitting Approach to the Lumbar Spine," Leon L. Wiltse et al., The Journal of Bone & Joint Surgery, vol. 50-A, No. 5, Jul. 1968 pp. 919-926.

Dynamic Reconstruction of the Spine, D.H. Kim et al., Thieme, New York 2006, Chapters 1, 2, 30, 31, 37-43.

International Search Report for PCT/US07/70981 dated Apr. 23, 2008, 7 pages.

International Search Report for PCT/US/2009/058466 dated Apr. 29, 2010, 13 pages.

International Search Report for PCT/US/2009/058460 dated Apr. 29, 2010, 11 pages.

International Search Report for PCT/US/2009/058470 dated Apr. 29, 2010, 12 pages.

International Search Report for PCT/US/2009/066567 dated Jul. 20, 2010, 9 pages.

* cited by examiner

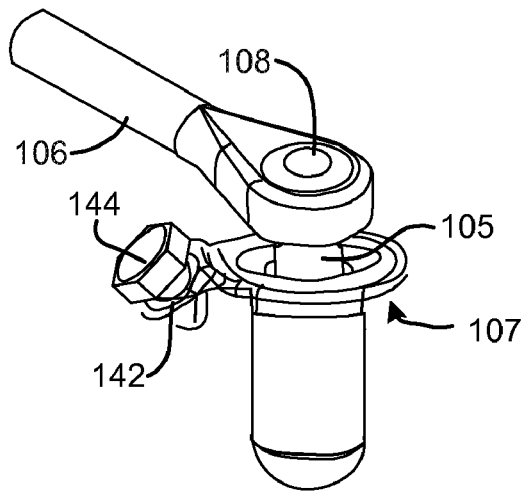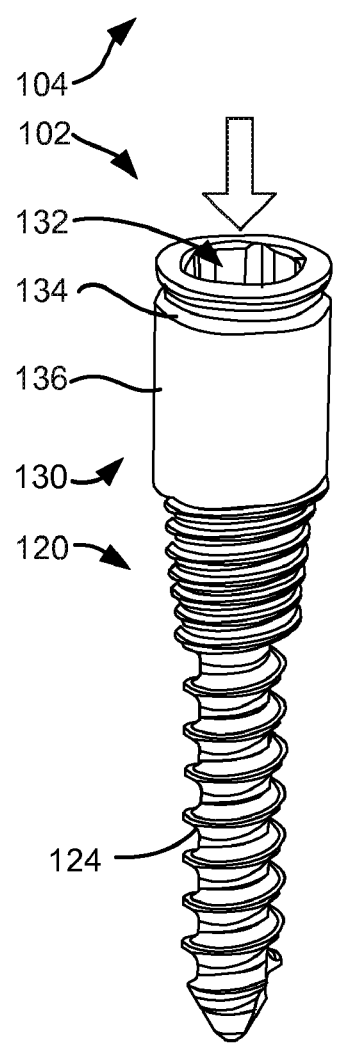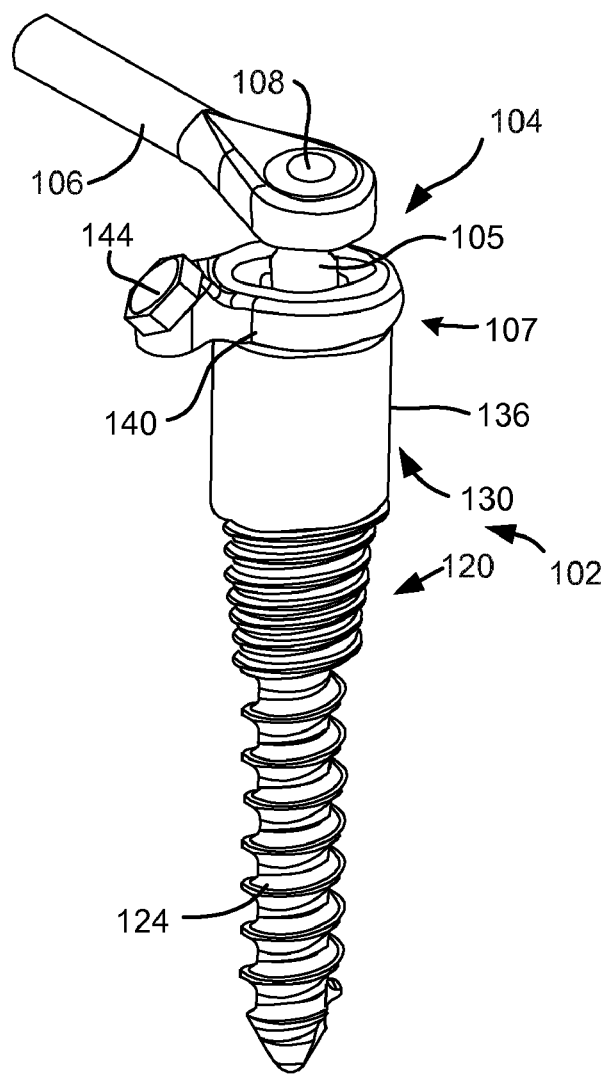
FIG. 1A  FIG. 1B

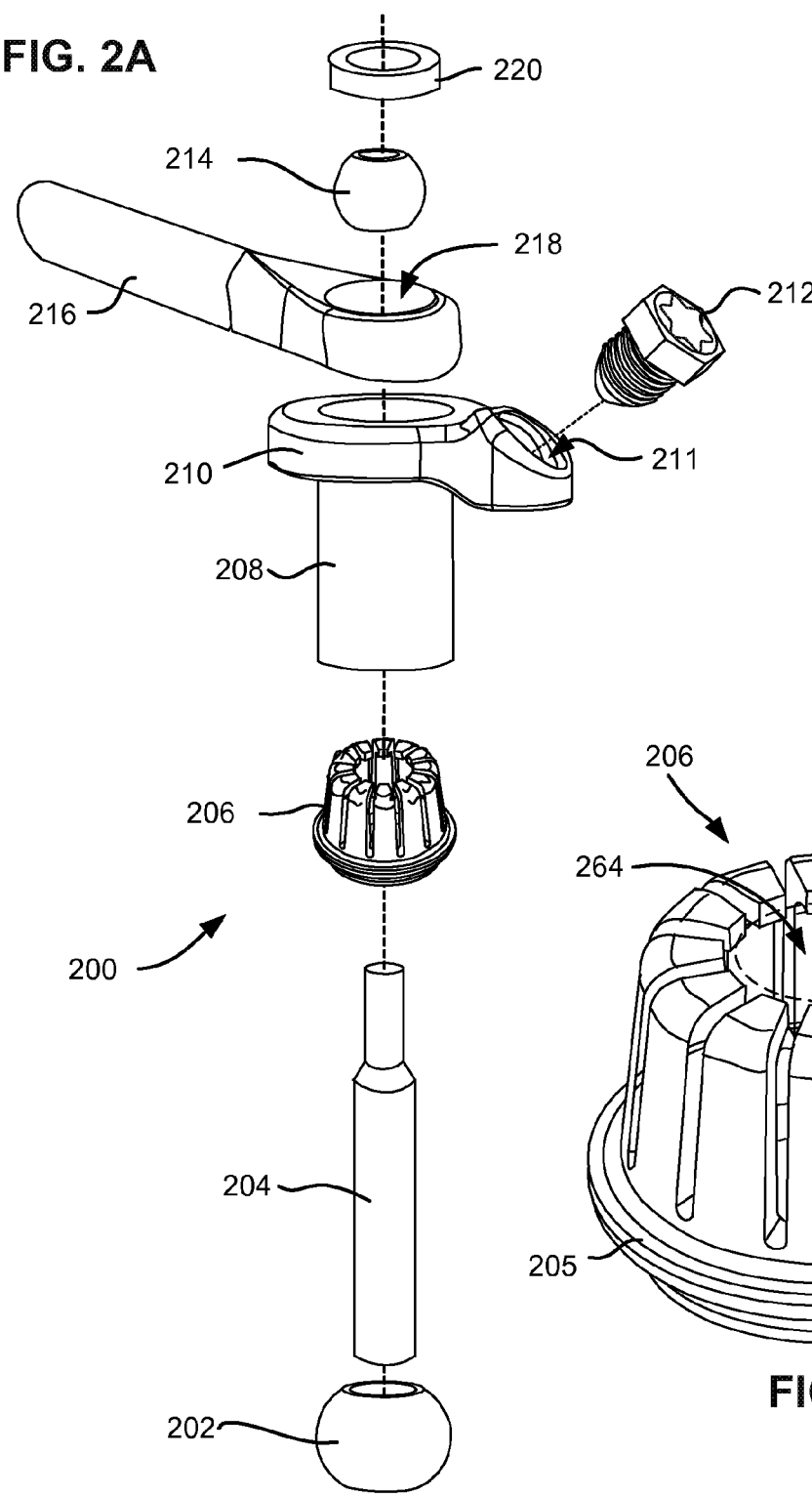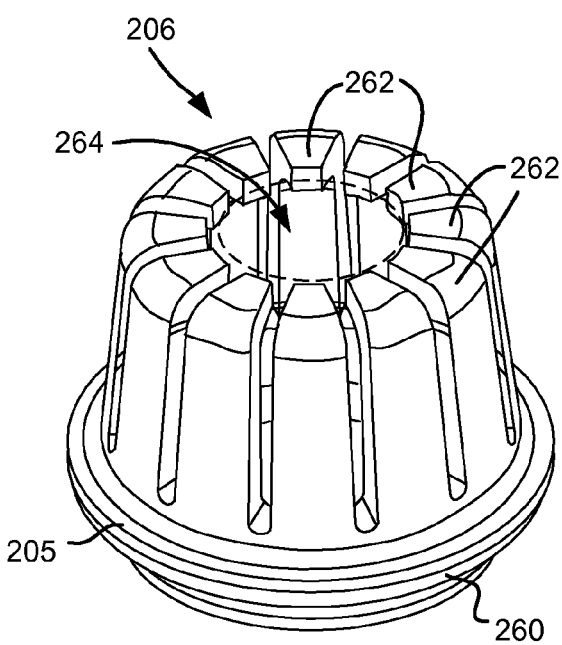

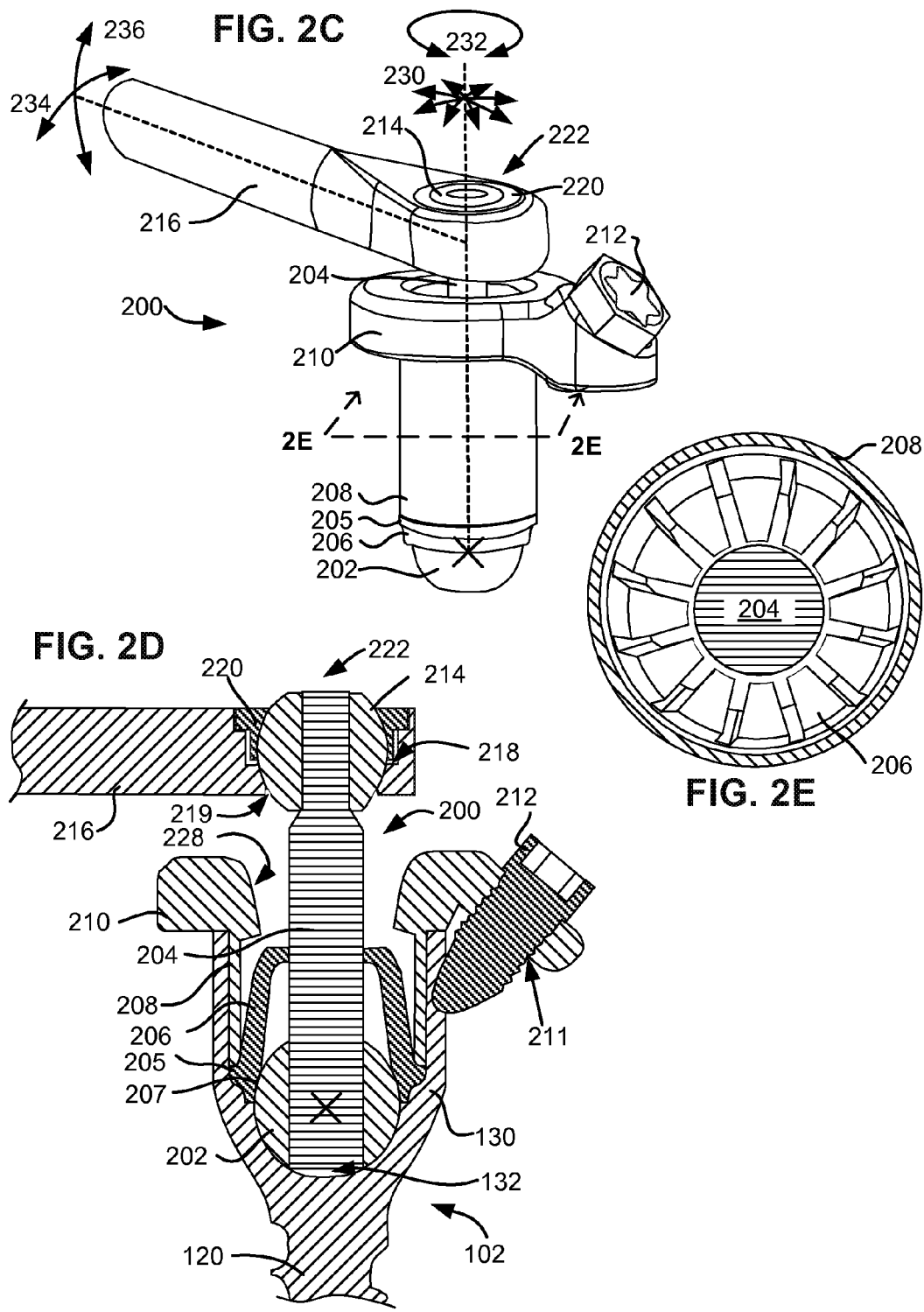

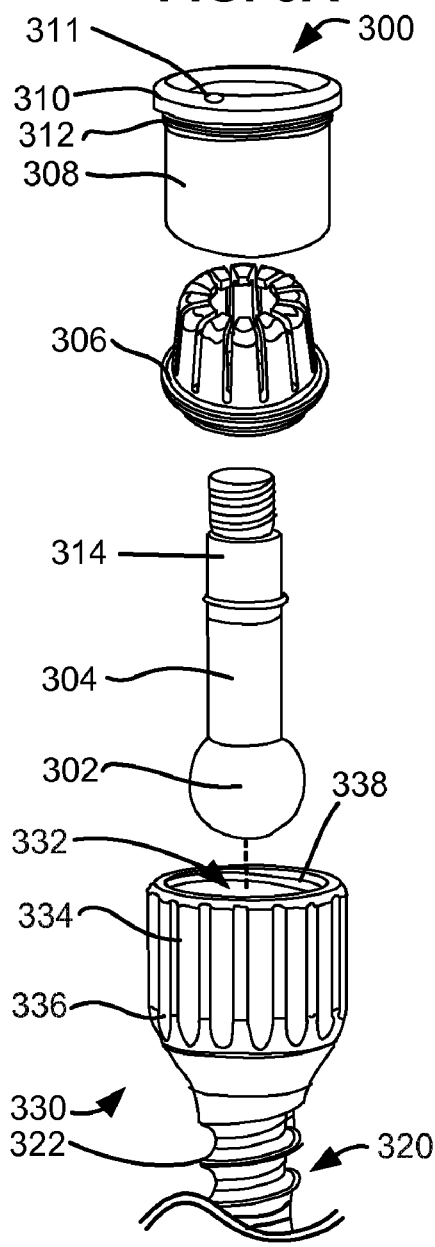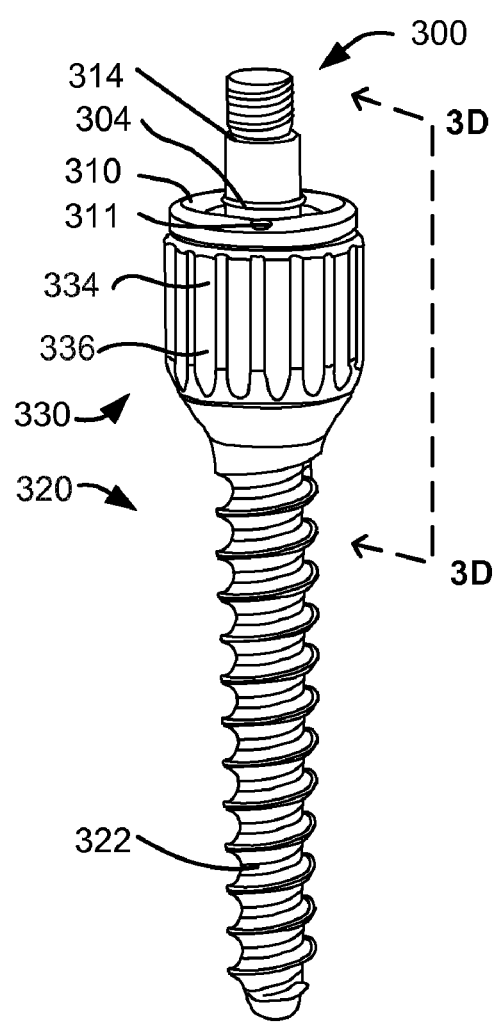

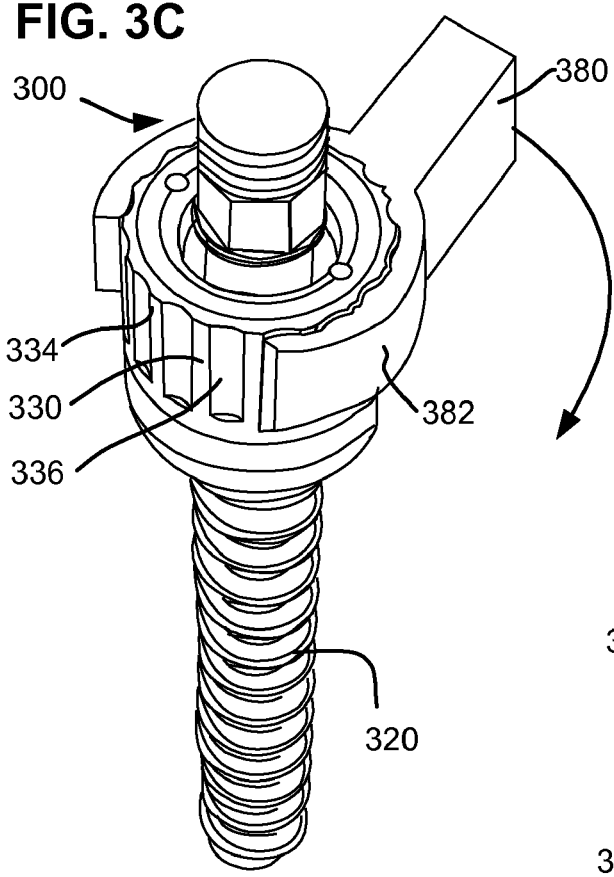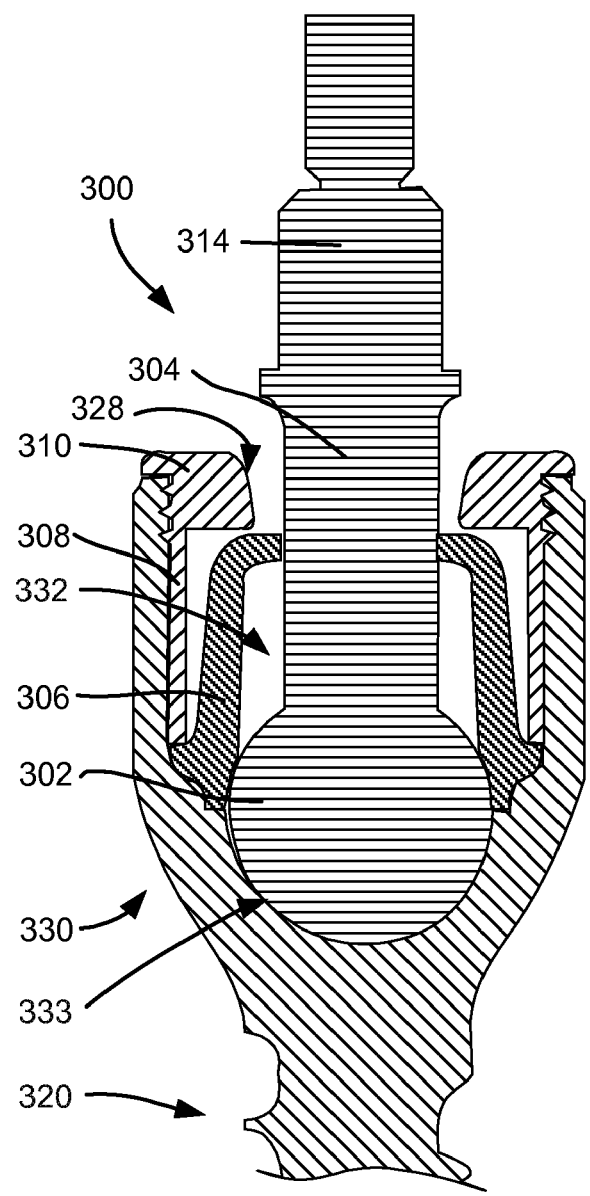

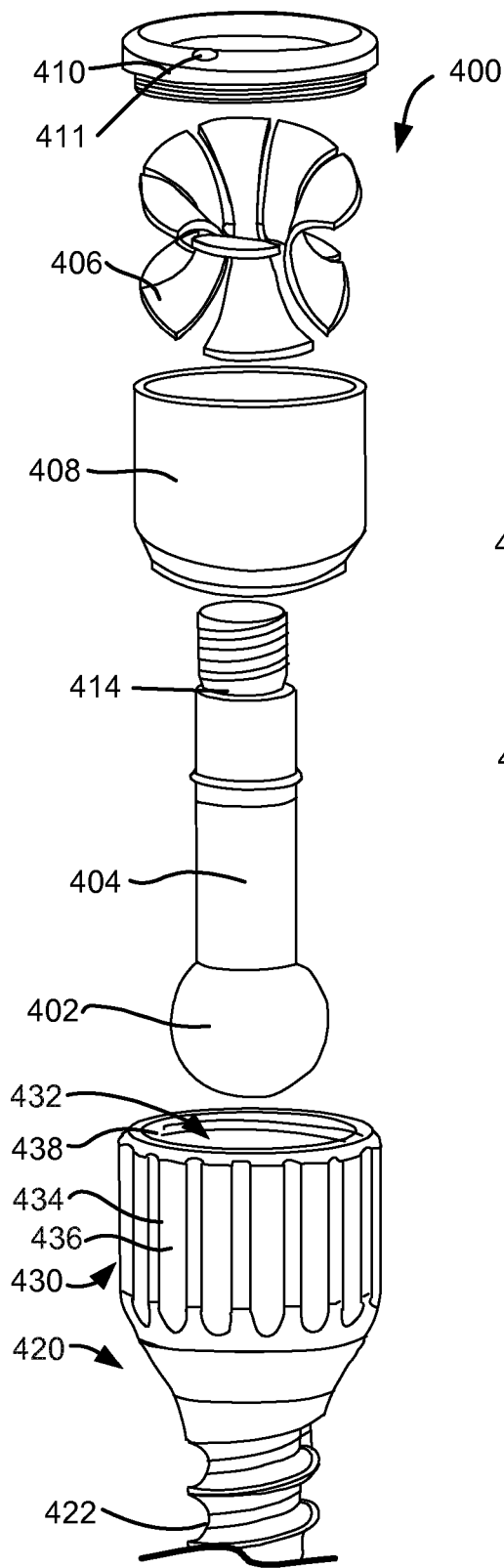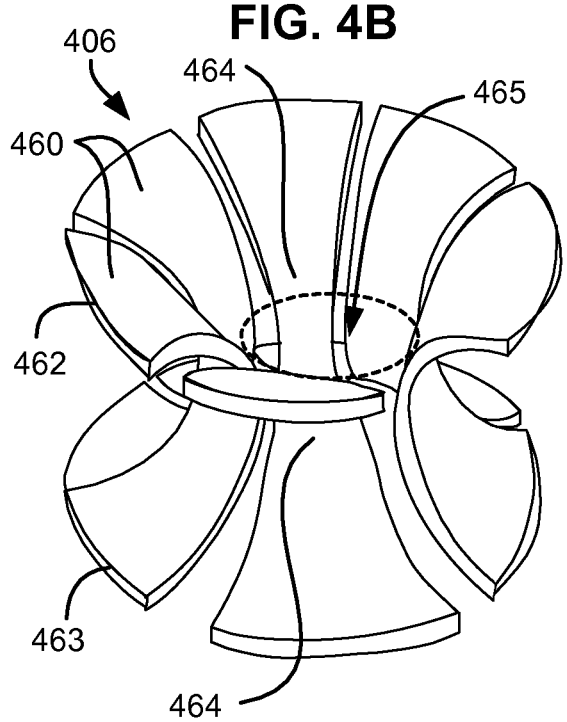

FIG. 5A
FIG. 5B
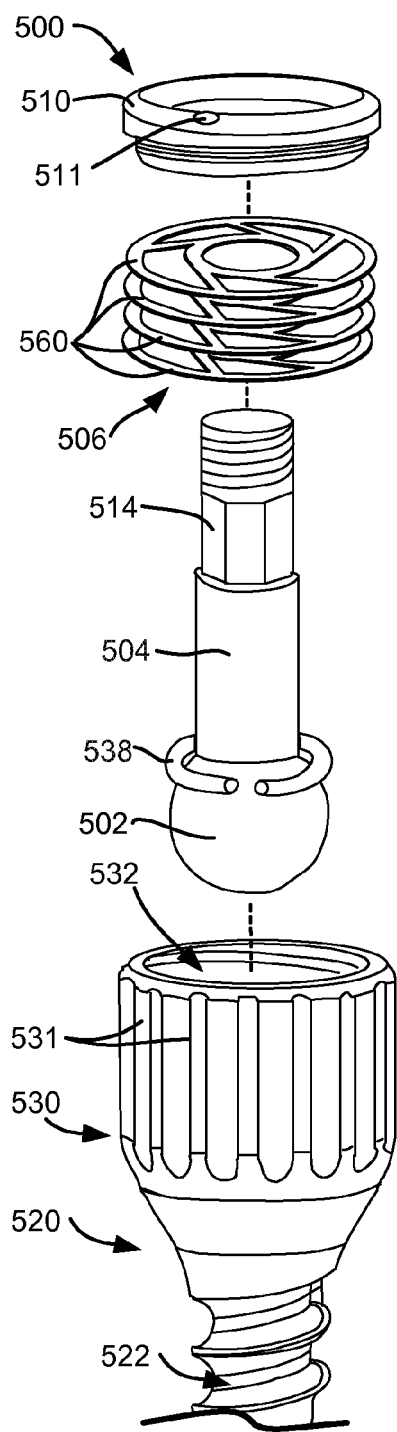
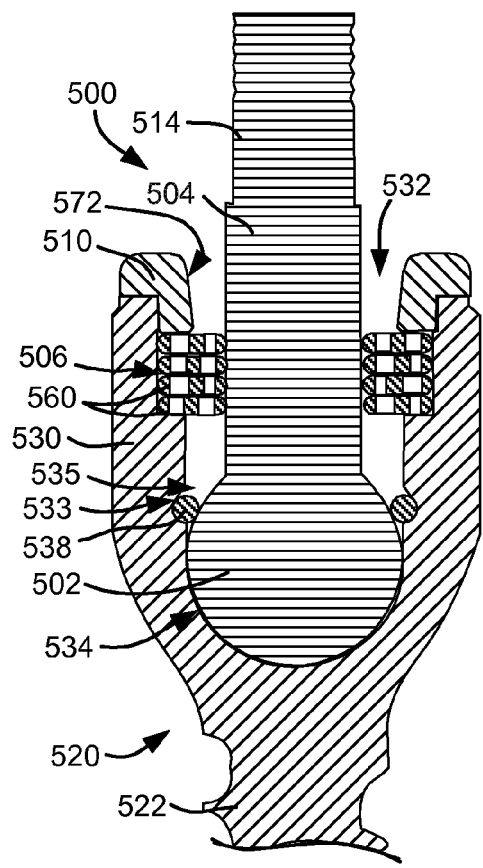

FIG. 5C
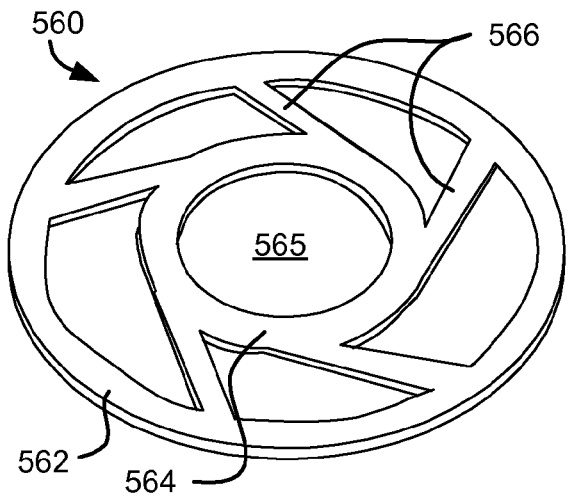
FIG. 5D
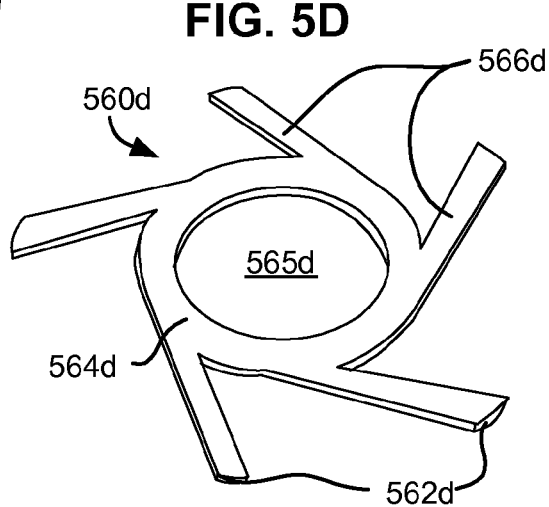
FIG. 5E
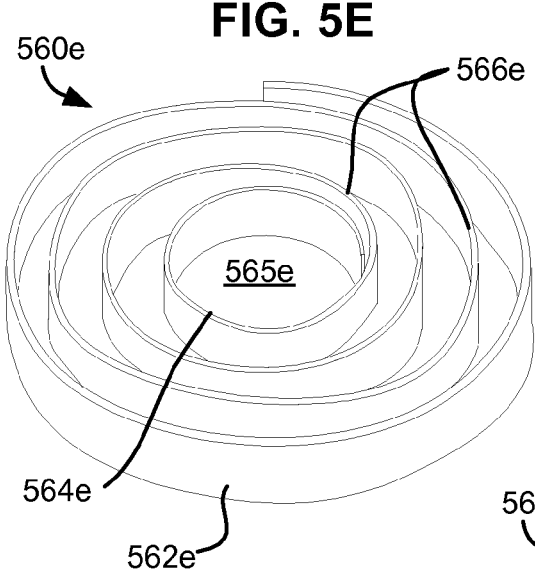
FIG. 5F
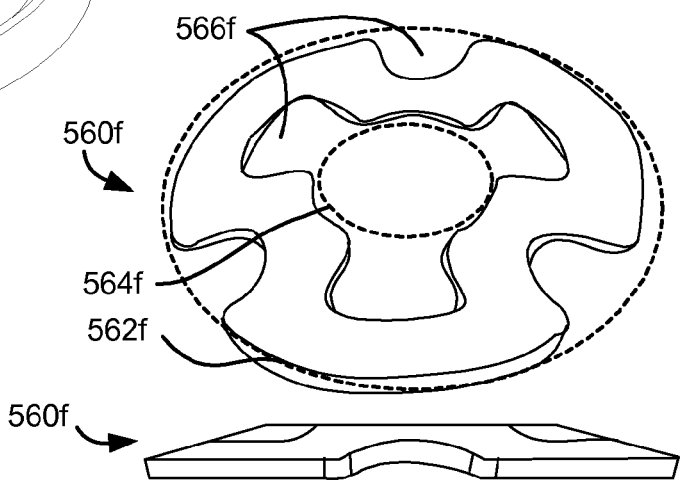
FIG. 5G

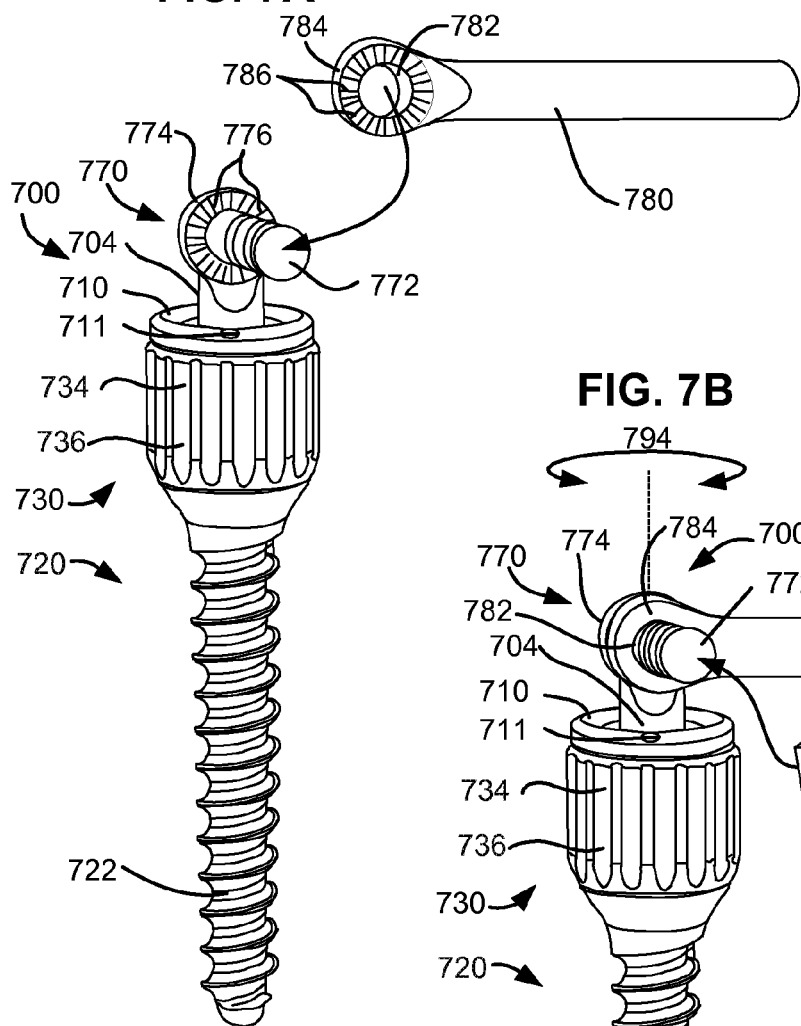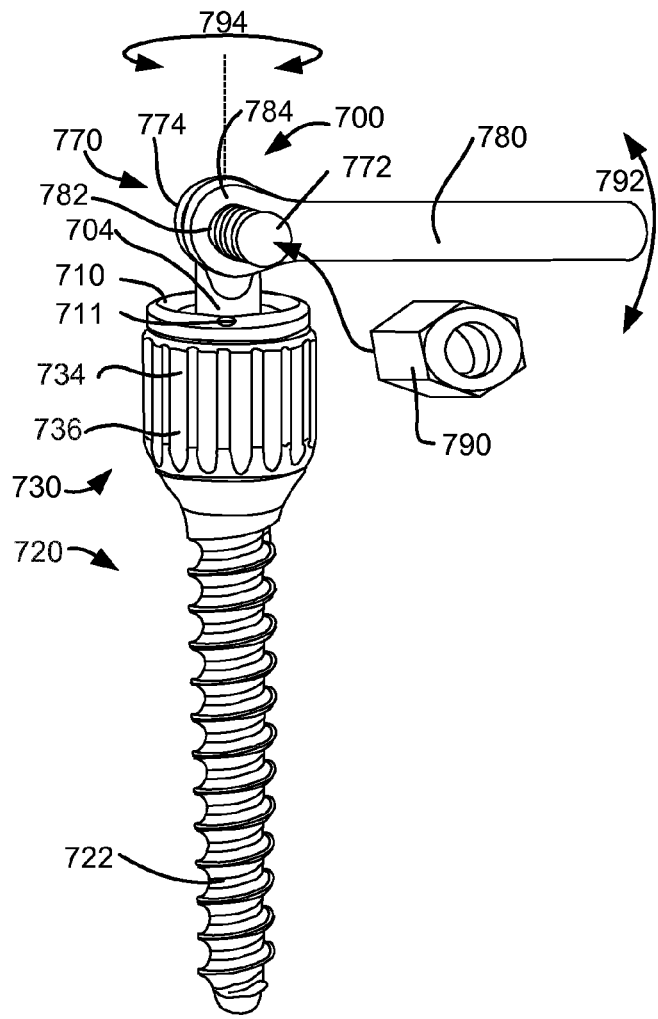

LOAD-SHARING ANCHOR HAVING A DEFLECTABLE POST AND CENTERING SPRING AND METHOD FOR DYNAMIC STABILIZATION OF THE SPINE

CLAIM TO PRIORITY

This application claims priority to the following patents and patent applications:

U.S. Provisional Application No. 61/100,593 filed Sep. 26, 2008, entitled "A Spine Implant With A Deflection Rod System Selectively Alignable And Selectively Lockable To A Bone Anchor And Method"; and U.S. Provisional Application No. 61/100,625 filed Sep. 26, 2008, entitled "Versatile Components And Methods For Dynamic Stabilization"; and U.S. Provisional Application No. 61/119,651 filed Dec. 3, 2008, entitled "Load-sharing Component Having A Deflectable Post And Methods For Dynamic Spinal Stabilization"; and U.S. Provisional Application No. 61/122,658 filed Dec. 15, 2008, entitled "Load-sharing Component Having A Deflectable Post And Methods For Dynamic Spinal Stabilization"; and U.S. Provisional Application No. 61/144,426 filed Jan. 13, 2009, entitled "Load-sharing Component Having A Deflectable Post And Methods For Dynamic Spinal Stabilization"; and U.S. Provisional Application No. 61/225,478 filed Jul. 14, 2009, entitled "Load-sharing Component Having A Deflectable Post And Methods For Dynamic Spinal Stabilization"; and U.S. Provisional Application No. 61/167,789 filed Apr. 8, 2009, entitled "Load-sharing Component Having A Deflectable Post And Spring And Methods For Dynamic Spinal Stabilization"; and U.S. Provisional Application No. 61/217,556 filed Jun. 1, 2009, entitled "Load-sharing Component Having A Deflectable Post And Axially-Compressible Spring And Methods For Dynamic Spinal Stabilization".

The present application is a continuation-in-part of U.S. patent application Ser. No. 12/130,395, filed May 30, 2008, entitled "A Deflection Rod System For A Dynamic Stabilization And Motion Preservation Spinal Implantation System And Method"which claims priority to U.S. Provisional Application No. 61/031,598 filed Feb. 26, 2008 and entitled "A Deflection Rod System For A Dynamic Stabilization And Motion Preservation Spinal Implantation System And Method".

The present application is also a continuation-in-part of U.S. patent application Ser. No. 12/130,095, filed May 30, 2008, entitled "A Spine Implant With A Deflection Rod System Including A Deflection Limiting Shield Associated With A Bone Screw And Method"which claims priority to U.S. Provisional Application No. 61/057,340 filed May 30, 2008, entitled "A Spine Implant With A Deflection Rod System Aligned With A Bone Anchor And Method".

All of the afore-mentioned patent applications are incorporated herein by reference in their entireties.

CROSS-REFERENCES TO RELATED APPLICATIONS

This application is related to all of the afore-mentioned patent applications. This application is also related to all of the following applications including:

U.S. patent application Ser. No. 12/566,478, filed Sep. 24, 2009, entitled "A Modular In-Line Deflection Rod And Bone Anchor System And Method For Dynamic Stabilization Of The Spine"; and U.S. patent application Ser. No. 12/566,485, filed Sep. 24, 2009, entitled "Versatile Polyaxial Connector Assembly And Method For Dynamic Stabilization Of The Spine"; and U.S. patent application Ser. No. 12/566,487 filed Sep. 24, 2009, entitled "Versatile Offset Polyaxial Connector And Method For Dynamic Stabilization Of The Spine"; and U.S. patent application Ser. No. 12/566,491 filed Sep. 24, 2009, entitled "Load-Sharing Bone Anchor Having A Deflectable Post and Method For Dynamic Stabilization Of The Spine"; and U.S. patent application Ser. No. 12/566,494 filed Sep. 24, 2009, entitled "Load-Sharing Component Having A Deflectable Post And Method For Dynamic Stabilization Of The Spine"; and U.S. patent application Ser. No. 12/566,498 filed Sep. 24, 2009, entitled "Load-Sharing Bone Anchor Having A Durable Compliant Member And Method For Dynamic Stabilization Of The Spine"; and U.S. patent application Ser. No. 12/566,504 filed Sep. 24, 2009, entitled "Load-Sharing Bone Anchor Having A Deflectable Post With A Compliant Ring And Method For Stabilization Of The Spine"; and U.S. patent application Ser. No. 12/566,507 filed Sep. 24, 2009, entitled "Load-Sharing Bone Anchor Having A Deflectable Post With A Compliant Ring And Method For Stabilization Of The Spine"; and U.S. patent application Ser. No. 12/566,509 filed Sep. 24, 2009, entitled "Load-Sharing Bone Anchor Having A Deflectable Post And Method For Stabilization Of The Spine"; and U.S. patent application Ser. No. 12/566,516 filed Sep. 24, 2009, entitled "Load-Sharing Bone Anchor Having A Deflectable Post And Method For Stabilization Of The Spine"; and U.S. patent application Ser. No. 12/566,519 filed Sep. 24, 2009, entitled "Dynamic Spinal Rod And Method For Dynamic Stabilization Of The Spine"; and U.S. patent application Ser. No. 12/566,522 filed Sep. 24, 2009, entitled "Dynamic Spinal Rod Assembly And Method For Dynamic Stabilization Of The Spine"; and U.S. patent application Ser. No. 12/566,529 filed Sep. 24, 2009, entitled "Configurable Dynamic Spinal Rod And Method For Dynamic Stabilization Of The Spine"; and U.S. patent application Ser. No. 12/566,531 filed Sep. 24, 2009, entitled "A Spinal Prosthesis Having A Three Bar Linkage For Motion Preservation And Dynamic Stabilization Of The Spine"; and U.S. patent application Ser. No. 12/566,534 filed Sep. 24, 2009, entitled "Surgical Tool And Method For Implantation of A Dynamic Bone Anchor"; and U.S. patent application Ser. No. 12/566,547 filed Sep. 24, 2009, entitled "Surgical Tool And Method For Connecting A Dynamic Bone Anchor and Dynamic Vertical Rod"; and U.S. patent application Ser. No. 12/566,551 filed Sep. 24, 2009, entitled "Load-Sharing Bone Anchor Having A Deflectable Post And Centering Spring And Method For Dynamic Stabilization Of The Spine"; and U.S. patent application Ser. No. 12/566,553 filed Sep. 24, 2009, entitled "Load-Sharing Component Having A Deflectable Post And Centering Spring And Method For Dynamic Stabilization Of The Spine"; and U.S. patent application Ser. No. 12/566,559 filed Sep. 24, 2009, entitled "Load-Sharing Bone Anchor Having A Deflectable Post And Axial Spring And Method For Dynamic Stabilization Of The Spine".

All of the afore-mentioned patent applications are incorporated herein by reference in their entireties.

BACKGROUND OF INVENTION

Back pain is a significant clinical problem and the costs to treat it, both surgical and medical, are estimated to be over $2 billion per year. One method for treating a broad range of degenerative spinal disorders is spinal fusion. Implantable medical devices designed to fuse vertebrae of the spine to treat have developed rapidly over the last decade. However, spinal fusion has several disadvantages including reduced range of motion and accelerated degenerative changes adjacent the fused vertebrae.

Alternative devices and treatments have been developed for treating degenerative spinal disorders while preserving motion. These devices and treatments offer the possibility of treating degenerative spinal disorders without the disadvantages of spinal fusion. However, current devices and treatments suffer from disadvantages e.g., complicated implantation procedures; lack of flexibility to conform to diverse patient anatomy; the need to remove tissue and bone for implantation; increased stress on spinal anatomy; insecure anchor systems; poor durability, and poor revision options. Consequently, there is a need for new and improved devices and methods for treating degenerative spinal disorders while preserving motion.

SUMMARY OF INVENTION

The present invention includes a spinal implant system and methods that can dynamically stabilize the spine while providing for the preservation of spinal motion. Embodiments of the invention provide a dynamic stabilization system which includes: versatile components, adaptable stabilization assemblies, and methods of implantation. An aspect of embodiments of the invention is the ability to stabilize two, three and/or more levels of the spine by the selection of appropriate components of embodiments of the invention for implantation in a patient. Another aspect of embodiments of the invention is the ability to accommodate particular anatomy of the patient by providing a system of versatile components which may be customized to the anatomy and needs of a particular patient and procedure. Another aspect of the invention is to facilitate the process of implantation and minimize disruption of tissues during implantation.

Thus, the present invention provides new and improved systems, devices and methods for treating degenerative spinal disorders by providing and implanting a dynamic spinal stabilization assembly which supports the spine while preserving motion. These and other objects, features and advantages of the invention will be apparent from the drawings and detailed description which follow.

BRIEF DESCRIPTION OF THE DRAWINGS

FIGS. 1A and 1B are perspective views of a deflection system component mounted to an anchor system component according to an embodiment of the present invention.

FIG. 2A is an exploded view of a deflection rod according to an embodiment of the present invention.

FIG. 2B is an enlarged view of the spring of FIG. 2A

FIG. 2C is a perspective view of the deflection rod of FIG. 2A, as assembled.

FIG. 2D is a sectional view of the deflection rod of FIGS. 2A and 2C.

FIG. 2E is a partial sectional view of the deflection rod of FIGS. 2A and 2C.

FIG. 3A is an exploded view of an alternative deflection rod according to an embodiment of the present invention.

FIG. 3B is a perspective view of the deflection rod of FIG. 3A, as assembled.

FIG. 3C is a perspective view illustrating engagement of a bone anchor by a driver.

FIG. 3D is a sectional of the assembled deflection rod of FIG. 3B.

FIG. 4A is an exploded view of an alternative deflection rod according to an embodiment of the present invention.

FIG. 4B is an enlarged view of the spring of the deflection rod of FIG. 4A.

FIG. 5A is an exploded view of an alternative deflection rod according to an embodiment of the present invention.

FIG. 5B is a sectional view of the deflection rod of FIG. 5A, as assembled.

FIG. 5C is an enlarged view of a spring element of the deflection rod of FIG. 5A.

FIGS. 5D-5G show views of alternative spring elements suitable for use in the deflection rod of FIGS. 5A and 5B.

FIGS. 7A and 7B are perspective views of an alternate mount for connecting a deflection rod to a vertical rod according to an embodiment of the present invention.

DETAILED DESCRIPTION OF THE PREFERRED EMBODIMENTS

Figure 1C:
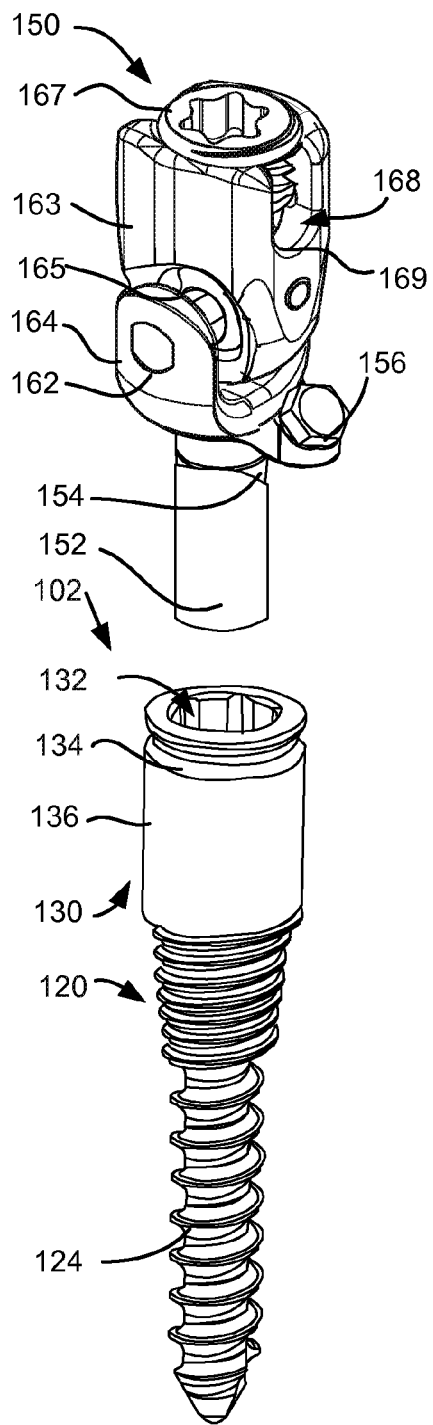
FIG. 1C is a perspective view of a connection system component mounted to an anchor system component according to an embodiment of the present invention.

The present invention includes a versatile spinal implant system and methods which can dynamically stabilize the spine while providing for the preservation of spinal motion. Alternative embodiments can be used for spinal fusion. An aspect of the invention is restoring and/or preserving the natural motion of the spine including the quality of motion as well as the range of motion. Still, another aspect of the invention is providing for load sharing and stabilization of the spine while preserving motion.

Another aspect of the invention is to provide a modular system which can be customized to the needs of the patient. Another aspect of embodiments of the invention is the ability to stabilize two, three and/or more levels of the spine by the selection of appropriate components for implantation in a patient. Another aspect of the invention is the ability to provide for higher stiffness and fusion at one level or to one portion of the spine while allowing for lower stiffness and dynamic stabilization at another adjacent level or to another portion of the spine. Embodiments of the invention allow for fused levels to be placed next to dynamically-stabilized levels. Such embodiments of the invention enable vertebral levels adjacent to fusion levels to be shielded by providing a transition from a rigid fusion level to a dynamically stable, motion preserved, and more mobile level.

Embodiments of the present invention provide for assembly of a dynamic stabilization system which supports the spine while providing for the preservation of spinal motion. The dynamic stabilization system has an anchor system, a deflection system, a vertical rod system and a connection system. The anchor system anchors the construct to the spinal anatomy. The deflection system provides dynamic stabilization while reducing the stress exerted upon the bone anchors and spinal anatomy. The vertical rod system connects different levels of the construct in a multilevel assembly and may in some embodiments include compound deflection rods. The connection system includes coaxial connectors and offset connectors which adjustably connect the deflection system, vertical rod system and anchor system allowing for appropriate, efficient and convenient placement of the anchor system relative to the spine. Alternative embodiments can be used for spinal fusion.

Embodiments of the invention include a construct with an anchor system, a deflection system, a vertical rod system and a connection system. The deflection system provides dynamic stabilization while reducing the stress exerted upon the bone anchors and spinal anatomy. The anchor system anchors the deflection system to the spine. The connection system connects the deflection system to the vertical rod system. The vertical rod system connects dynamic stabilization system components on different vertebra to provide load sharing and dynamic stabilization.

Embodiments of the present invention include a deflection rod which provides load sharing while preserving range of motion and reducing stress exerted upon the bone anchors and spinal anatomy. The deflection rod includes a deflectable post mounted within a bone anchor. Deflection of the deflectable post is controlled by a spring. A contact surface of the deflection rod is positioned to limit deflection of the deflectable post. The force-deflection properties of the deflection rod may be adapted and/or customized to the anatomy and functional requirements of the patient by changing the properties of the spring. Different deflection rods having different force-deflection properties may be utilized in different patients or at different spinal levels within the same patient depending upon the anatomy and functional requirements. Moreover deflection rods may be utilized at a spinal level with fusion at an adjacent spinal level.

Common reference numerals are used to indicate like elements throughout the drawings and detailed description; therefore, reference numerals used in a drawing may or may not be referenced in the detailed description specific to such drawing if the associated element is described elsewhere. The first digit in a reference numeral indicates the series of figures in which the referenced item first appears.

The terms "vertical" and "horizontal" are used throughout the detailed description to describe general orientation of structures relative to the spine of a human patient that is standing. This application also uses the terms proximal and distal in the conventional manner when describing the components of the spinal implant system. Thus, proximal refers to the end or side of a device or component closest to the hand operating the device, whereas distal refers to the end or side of a device furthest from the hand operating the device. For example, the tip of a bone screw that enters a bone would conventionally be called the distal end (it is furthest from the surgeon) while the head of the screw would be termed the proximal end (it is closest to the surgeon).

Dynamic Stabilization System

FIGS. 1A-1F introduce components of a dynamic stabilization system according to an embodiment of the present invention. The components include anchor system components, deflection rods, vertical rods and connection system components, including for example coaxial and offset connectors. The components may be implanted and assembled to form a dynamic stabilization system appropriate for the anatomical and functional needs of a patient.

FIG. 1A shows a bone anchor 102 and a deflection rod 104 connected to a vertical rod 106 by a ball joint 108. In other embodiments, the vertical rod may be mounted directly to the deflection rod. Deflection rod 104 is an example of a component of the deflection system. Deflection rod 104 is a component having controlled flexibility which allows for load sharing. The deflection rod 104 provides stiffness and support where needed to support the loads exerted on the spine during normal spine motion, which loads, the soft tissues of the spine are no longer able to accommodate since these spine tissues are either degenerated or damaged. Load sharing is enhanced by the ability to select the appropriate stiffness of the deflection rod in order to match the load sharing characteristics desired. For embodiments of this invention, the terms "deflection rod" and "loading rod" can be used interchangeably. Deflection rods, deflection rod mountings and alternative deflection rods are described in more detail below.

Deflection rod 104 includes a deflectable post 105 which may deflect relative to a collar 107. Collar 107 is adapted to secure the deflectable post 105 to bone anchor 102. Collar 107 secures deflection rod 104 within cavity 132 of bone anchor 102. In other embodiments, the deflection rod may be integrated with a bone anchor. When received in cavity 132, collar 107 is secured into a fixed position relative to bone anchor 102. Deflectable post 105 may still deflect in a controlled manner relative to bone anchor 102 thereby provide for load sharing while preserving range of motion of the patient. The stiffness/flexibility of deflection of the deflectable post 105 relative to the bone anchor 102 may be controlled and/or customized as will be described below.

As shown in FIG. 1A, collar 107 is designed to secure deflection rod 104 within a cavity 132 of bone anchor 102. As shown in FIG. 1A, a threaded aperture 142 extends obliquely through collar 107. The threaded aperture 142 receives a locking set screw 144 which, when seated (FIG. 1B), engages the housing 130 of bone anchor 102. Locking set screw 144 is positioned within threaded aperture 142 through collar 107. The locking set screw 144 thereby secures the deflection rod 104 in place within the housing 130 of bone anchor 102.

Bone anchor 102 is an example of a component of the anchor system. Bone anchor 102 includes a bone screw 120 and housing 130. As shown in FIG. 1A, bone anchor 102 is a bone screw 120 having one or more threads 124 which engage a bone to secure the bone anchor 102 onto a bone. The anchor system may include one or more alternative bone anchors known in the art e.g. bone hooks, expanding devices, barbed devices, threaded devices, adhesive and other devices capable of securing a component to bone instead of or in addition to bone screw 120.

As shown in FIG. 1A, deflection rod 104 is oriented in a co-axial, collinear or parallel orientation to bone anchor 102. This arrangement simplifies implantation, reduces trauma to structures surrounding an implantation site, and reduces system complexity. Arranging the deflection rod 104 co-axial with the bone anchor 102 can substantially transfer a moment (of) force applied by the deflectable post 105 from a moment force tending to pivot or rotate the bone anchor 102 about the axis of the shaft, to a moment force tending to act perpendicular to the axis of the shaft. The deflection rod can, thereby, effectively resist repositioning of the deflection rod and/or bone anchor 102 without the use of locking screws or horizontal bars to resist rotation. Further examples of coaxial deflection rods are provided below. Each of the deflection rods described herein may be used as a component of a dynamic stabilization system.

As shown in FIG. 1A, bone anchor 102 includes a housing 130 at the proximal end. Housing 130 includes a cavity 132 for receiving deflection rod 104. Cavity 132 is coaxial with threaded bone screw 120. Housing 130 also comprises a groove 134 for securing deflection rod 104 within housing 130. As shown in FIG. 1A, groove 134 is located at the proximal end of housing 130. Groove 134 is designed to be engaged by the locking mechanism of a component mounted within cavity 132. For example, groove 134 is designed to be engaged by locking set screw 144 of deflection rod 104. When deflection rod 104 has been positioned within cavity 132 of bone anchor 102 as shown in FIG. 1B, locking set screw 144 is tightened to engage groove 134 of housing 130, thus, securing deflection rod 104 within housing 130. Alternative mechanisms and techniques may be used to secure the deflection rod to the bone anchor including for example, welding, soldering, bonding, and/or mechanical fittings including threads, snap-rings, locking washers, cotter pins, bayonet fittings or other mechanical joints.

Bone anchor 102 also includes a coupling 136 to which other components may be mounted. As shown in FIG. 1A, coupling 136 is the external cylindrical surface of housing 130. Housing 130 thus provides two mounting positions, one coaxial mounting position and one external (or offset) mounting position. Thus, a single bone anchor 102 can serve as the mounting point for one, two or more components. A deflection rod 104 may be coaxially mounted in the cavity 132 of the housing and one or more additional components may be externally mounted to the outer surface of the housing-coupling 136. For example, a component of the connection system may be mounted to the outer surface 136 of the housing—such a connector may be called an offset head or offset connector. In some applications, a component of the connection system may be coaxially-mounted in the cavity 132 in place of a deflection rod 104—such a connector may be called a coaxial head or coaxial connector.

It is desirable to have a range of different connectors which are compatible with the anchor system and deflection system. The connectors may have different attributes, including for example, different degrees of freedom, range of motion, and amount of offset, which attributes may be more or less appropriate for a particular relative orientation and position of two bone anchors and/or patient anatomy. It is desirable that each connector be sufficiently versatile to connect a vertical rod to a bone anchor in a range of positions and orientations while being simple for the surgeon to adjust and secure. It is desirable to provide a set of connectors which allows the dynamic stabilization system to be assembled in a manner that adapts a particular dynamic stabilization assembly to the patient anatomy rather than adapting the patient anatomy for implantation of the assembly (for example by removing tissue\bone to accommodate the system). In a preferred embodiment, the set of connectors comprising the connection system have sufficient flexibility to allow the dynamic stabilization system to realize a suitable dynamic stabilization assembly in all situations that will be encountered within the defined patient population.

In some embodiments of the present invention, a connection system component, e.g. a polyaxial connector may be mounted in the cavity 132 of a bone anchor 102 to secure the bone anchor to a vertical rod. For example, FIG. 1C shows coaxial head 150 which is a polyaxial connector which is coaxially mounted within the cavity 132 of the housing 130 of bone anchor 102. Coaxial head 150 is an example of a coaxial head or coaxial connector. Bone anchor 102 is the same bone anchor previously described with respect to FIGS. 1A and 1B. Coaxial head 150 comprises a rod 152 which is designed to fit within cavity 132 of housing 130. Coaxial head 150 also comprises a collar 154 and locking set screw 156. Locking set screw 156 is configured to engage groove 134 of bone anchor 102 in the same way as locking set screw 144 of deflection rod 104. Rod 152 and cavity 132 may, in some case, be circular in section (e.g. cylindrical), in which case rod 152 can rotate within cavity 132 until locked into place by fastener 134. In alternative embodiments, rod 152 may be polygonal in section such that it fits in one of a fixed number of possible positions.

Referring again to FIG. 1C, attached to rod 152 of coaxial head 150 is a yoke 164. Yoke 164 is connected to a ball 165 by a hexagonal pin 162. A saddle 163 is also mounted to ball 165 such that saddle 163 can pivot about two orthogonal axes relative to yoke 164. Saddle 163 has an aperture 168 through which a vertical rod may be passed. On one side of aperture 168 is a plunger 169. On the other side of aperture 168 is a locking set screw 167. When a vertical rod 106 (not shown) is positioned within aperture 168 and locking set screw 167 is tightened down, the locking set screw 167 forces the vertical rod 106 down onto the plunger 169. Plunger 169 is, in turn, forced down by the vertical rod 106 against ball 165. Plunger 169 engages ball 165, and ball 165 engages hexagonal pin 162, to lock saddle 163 in position relative to yoke 164 and secure a rod (e.g. vertical rod 106) to saddle 163. In this way, tightening set screw 167 secures the vertical rod 106 to the coaxial head 150 and also locks orientation of the coaxial head 150.

The ability to coaxially mount coaxial head 150 to a bone anchor 102 has several advantages over a standard polyaxial bone screw in which a polyaxial connector is an integral part of the device and may not be removed or exchanged. The bone anchor 102 is simpler to install and there is no risk of damage to the polyaxial connector during installation. A single coaxial head 150 can be manufactured and designed to mount to a range of different bone anchors thus allowing bone anchors to be selected as appropriate for the patient anatomy. After the bone anchor is installed the orientation of the yoke 164 can be adjusted without changing the screw depth (this is not possible in a standard polyaxial bone screw without also turning the screw). After the bone anchor is implanted, one of a range of different coaxial heads may be installed without requiring removal of the bone anchor. Likewise, if a revision is required the coaxial head may be exchanged for a different component without necessitating removal of the bone anchor 102.

Figure 1D:
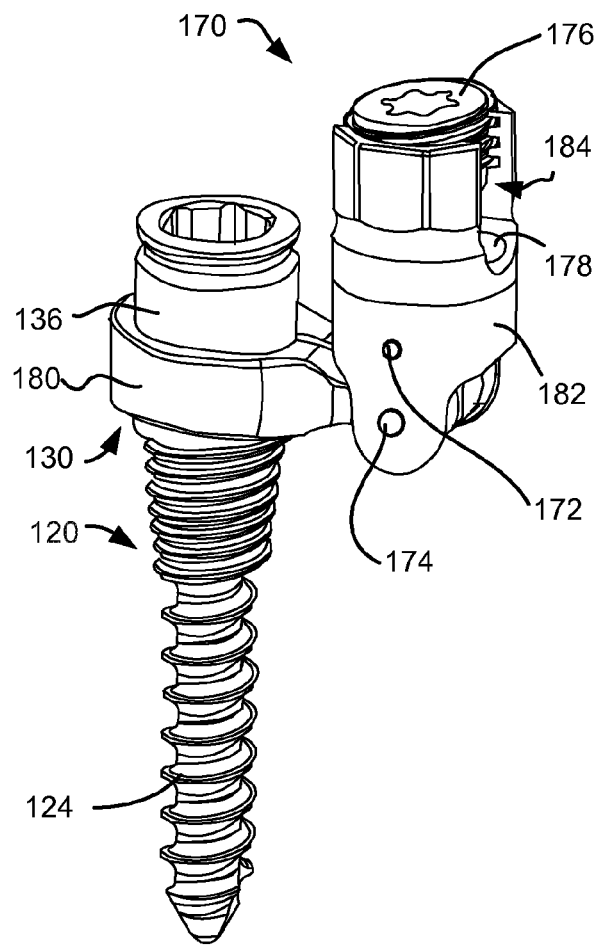
FIG. 1D is a perspective view of a different connection system component mounted to an anchor system component according to an embodiment of the present invention.

As described above, bone anchor 102 has a housing which can accept one coaxially-mounted component (e.g. a coaxial head) and one externally-mounted component (e.g. an offset connector). FIG. 1D shows a component of the connection system which may be mounted externally to the housing 130 of bone anchor 102 in conjunction with a coaxially-mounted component. FIG. 1D shows a perspective view of offset connector 170 mounted externally to housing 130 of bone anchor 102 in which a deflection rod 104 is coaxially mounted. Connector 170 may be termed an offset head or offset connector.

Offset connector 170 comprises six components and allows for two degrees of freedom of orientation and two degrees of freedom of position in connecting a vertical rod to a bone anchor. The six components of offset connector 170 are dowel pin 172, pivot pin 174, locking set screw 176, plunger 178, clamp ring 180 and saddle 182. Saddle 182 has a slot 184 sized to receive a rod which may be a vertical rod, e.g. vertical rod 106 of FIG. 1A. Locking set screw 176 is mounted at one end of slot 184 such that it may be tightened to secure a rod within slot 184.

Clamp ring 180 is sized such that, when relaxed it can slide freely up and down the housing 130 of bone anchor 102 and rotate around the housing 130. However, when locking set screw 176 is tightened on a rod, the clamp ring 180 grips the housing and prevents the offset connector 170 from moving in any direction. Saddle 182 is pivotably connected to clamp ring 180 by pivot pin 174. Saddle 182 can pivot about pivot pin 174. However, when locking set screw 176 is tightened on a rod, the plunger 178 grips the clamp ring 180 and prevents further movement of the saddle 182. In this way, operation of the single set screw 176 serves to lock the clamp ring 180 to the housing 130 of the bone anchor 102, fix saddle 182 in a fixed position relative to clamp ring 180 and secure a rod within the slot 184 of offset connector 170.

The above-described coaxial connector and offset connector are provided by way of example only. Alternative embodiments of coaxial heads and offset connectors can be found in U.S. Provisional Patent Application No. 61/100,625, filed Sep. 26, 2008 entitled "Versatile Assembly Components And Methods For A Dynamic Spinal Stabilization System" which is incorporated by reference. These coaxial heads and offset connectors may be used in conjunction with the components herein described to permit assembly of a dynamic stabilization system appropriate to the functional needs and anatomy of a particular patient. In addition screws having an integrated connector may also be utilized to anchor components of the dynamic stabilization system in fixed relationship to a vertebra, for example polyaxial screws.

The components of the dynamic stabilization system may be assembled and implanted in the spine of a patient to provide a multilevel dynamic stabilization assembly which provides dynamic stabilization of the spine and load sharing. In some embodiments, the first step is implantation of bone anchors in the vertebrae. In other embodiments, the bone anchors may be implanted with the deflection rod/connection component already installed and/or built in.

Figure 1E:
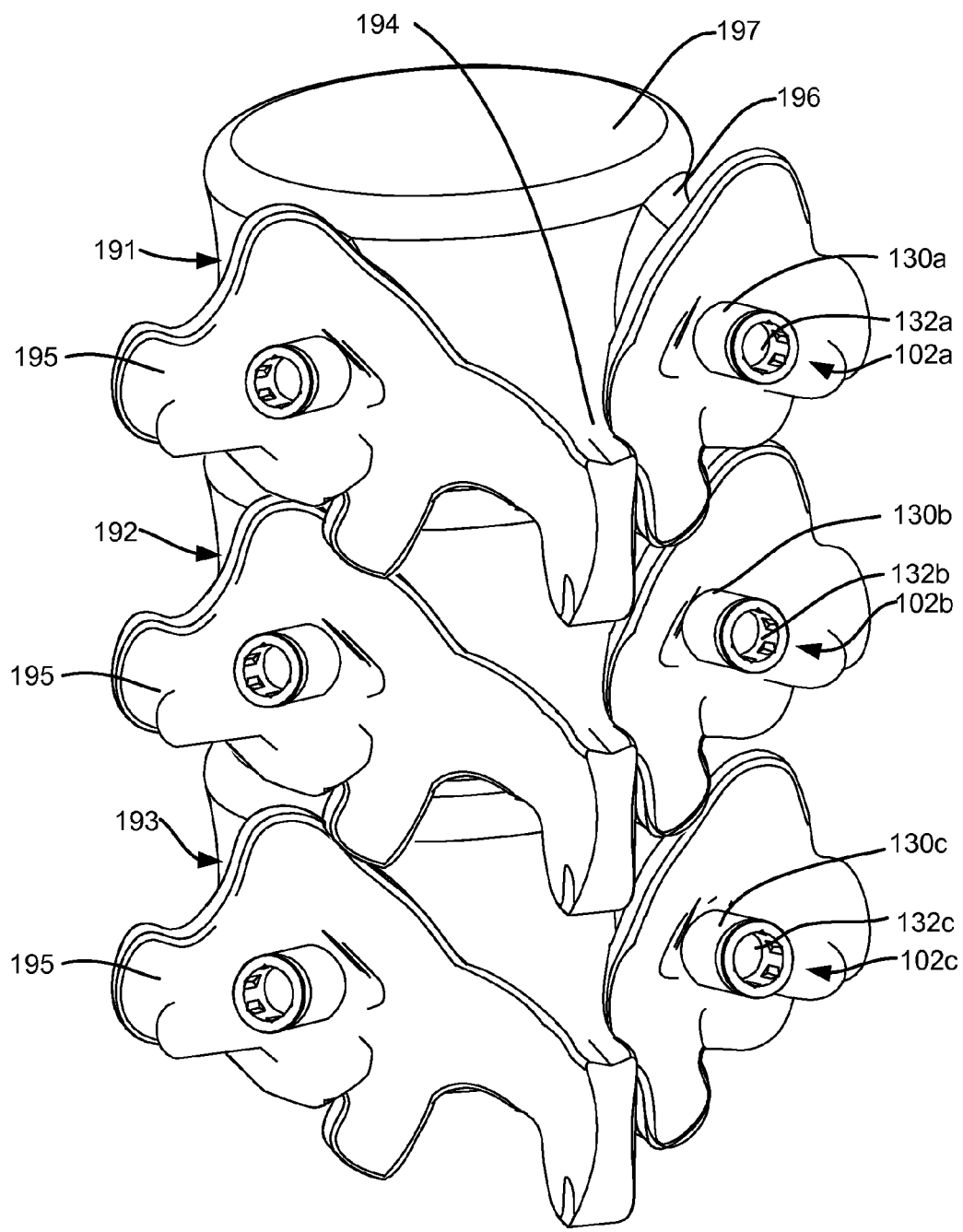
FIG. 1E is a posterior view of an anchor system for a multi-level dynamic stabilization assembly utilizing the anchor components of FIGS. 1A to 1D according to an embodiment of the present invention.

FIG. 1E, shows three adjacent vertebrae 191, 192 and 193. As a preliminary step, bone anchors 102a, 102b and 102c have been implanted in the vertebrae 191, 192 and 193 on the right side of the spinous process 194 between the spinous process 194 and the transverse process 195. A driver is inserted into the cavity 132a, 132b, 132c in order to drive the threaded portion of each bone anchor into the bone. In preferred procedures, the bone anchor is directed so that the threaded portion is implanted within one of the pedicles 196 angled towards the vertebral body 197. The threaded region of each bone anchor is fully implanted in the vertebrae 191, 192 and 193. A driver may alternatively and/or additionally engage the exterior surface of housing 130 in order to implant the bone anchor.

As shown in FIG. 1E, the housings 130a, 130b, 130c of each bone anchor remain partly or completely exposed above the surface of the vertebrae so that one or more of a connection system component and deflection component can be secured to each bone anchor 102a, 102b and 102c. Coaxial components may be coaxially-mounted inside each of cavities 132a, 132b, and 132c. Offset heads/connectors may also be externally-mounted to the outside surface of each of housings 130a, 130b and 130c. Note that bone anchors are also implanted on the left side of the spine.

Figure 1F:
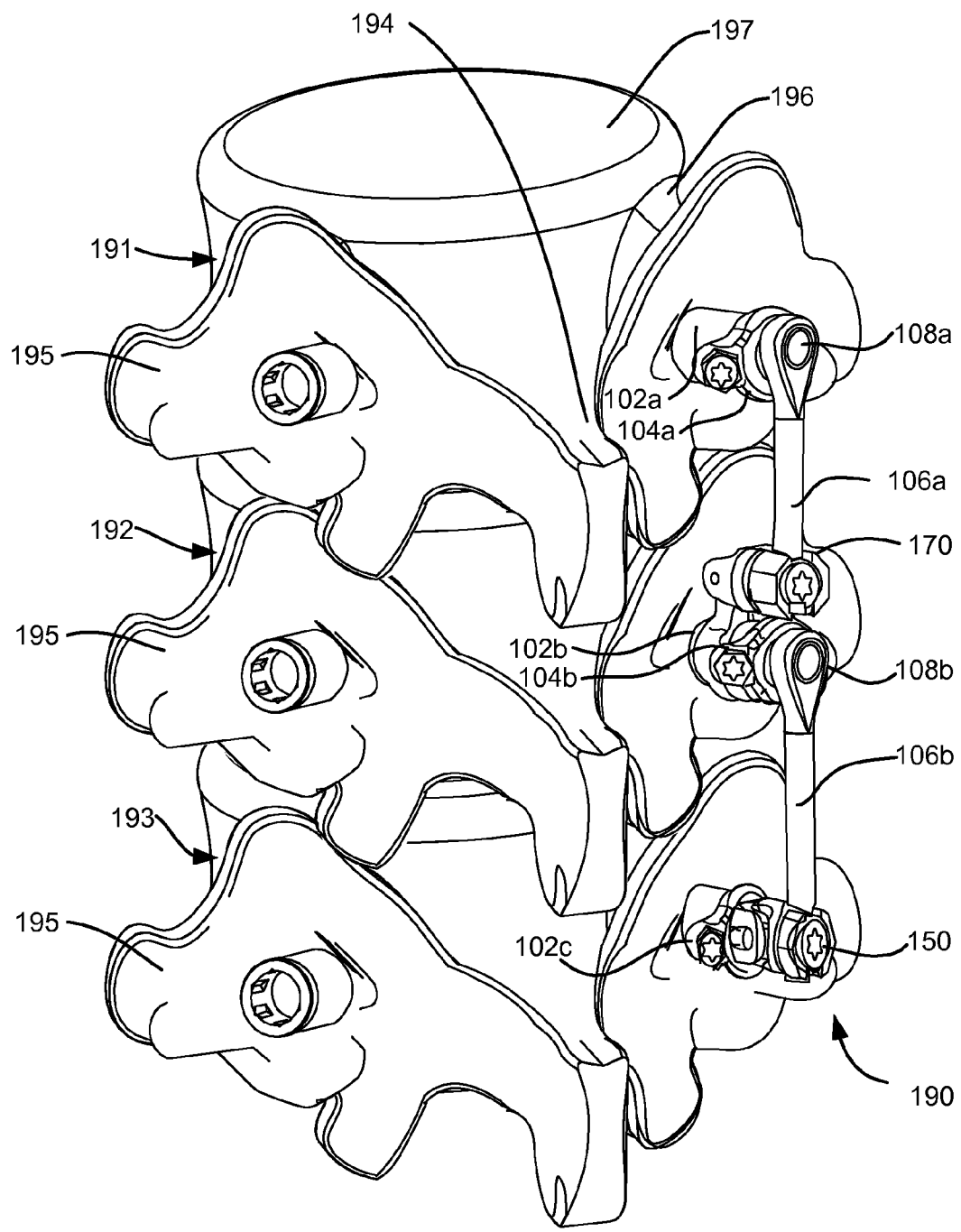
FIG. 1F is a posterior view of a multi-level dynamic stabilization assembly utilizing the components of FIGS. 1A to 1E according to an embodiment of the present invention.

After installation of the bone anchors, the deflection system components, vertical rod systems components and connection system components may be installed and assembled. FIG. 1F shows one way to assemble deflection system components and connection system components. As shown in FIG. 1F, a coaxial head 150 is installed in bone anchor 102c. An offset connector 170 is mounted externally to the housing of bone anchor 102b. A deflection rod 104a is coaxially mounted in the housing of bone anchor 102a. A deflection rod 104b is coaxially mounted in the housing of bone anchor 102b. A vertical rod 106a is connected at one end to deflection rod 104a by ball joint 108a. Vertical rod 106a is connected at the other end by in-line connector 170 to bone anchor 102b. A second vertical rod 106b is connected at one end to deflection rod 104b by ball joint 108b. Vertical rod 106b is connected at the other end by coaxial head 160 to bone anchor 102c.

The dynamic stabilization assembly 190 of FIG. 1F thus has a vertical rod 106a, 106b stabilizing each spinal level (191-192 and 192-193). Each of the vertical rods 106a, 106b is secured rigidly at one end to a bone anchor (102b, 102c). Each of the vertical rods 106a, 106b is secured at the other end by a ball joint to a deflection rod 108a, 108b thereby allowing for some movement and load sharing by the dynamic stabilization assembly. Offset connector 170 and coaxial head 150 permit assembly of dynamic stabilization assembly 190 for a wide range of different patient anatomies and/or placements of bone anchors 102a, 102b and 102c. An identical or similar dynamic stabilization assembly would preferably be implanted on the left side of the spine. It should be noted that dynamic stabilization assembly 190 does not require horizontal bars or locking screws thereby reducing the exposure of tissue and/or bone to foreign bodies compared to systems with this additional hardware. The dynamic stabilization assembly of FIG. 1F, thereby, has a small footprint, potentially reducing the amount of displacement of tissue and/or bone, reducing trauma to tissue and/or bone during surgery. Further, the smaller footprint can reduce the amount of tissue that needs to be exposed during implantation.

The particular dynamic stabilization assembly shown in FIG. 1F is provided by way of example only. It is an aspect of preferred embodiments of the present invention that a range of components be provided and that the components may be assembled in different combinations and organizations to create different assemblies suitable for the functional needs and anatomy of different patients. Also, deflection rods having different force deflection characteristics may be incorporated at different spinal levels in accordance with the anatomical and functional requirements. Dynamic stabilization may be provided at one or more motion segments and in some cases dynamic stabilization may be provided at one or more motion segments in conjunction with fusion at an adjacent motion segment. Particular dynamic stabilization assemblies may incorporate combinations of the bone anchors, vertical rods, deflection rods, offset and coaxial connectors described herein, in the related applications incorporated by reference, and standard spinal stabilization and/or fusion components, for example screws, rods and polyaxial screws.

Deflection Rods/Loading Rods

One feature of embodiments of the present invention is the load sharing and range of motion provided by the deflection system and deflection rods of the deflection system. The deflection rod provides stiffness and support where needed to support the loads exerted on the spine during normal spine motion thereby recovering improved spine function without sacrificing all motion. The deflection rod also isolates the anchor system components from forces exerted by the dynamic stabilization assembly; thereby reducing stress on the bone anchors and the bone to which they are attached. Moreover, by selecting the appropriate stiffness of the deflection rod to match the physiology of the patient and the loads that the patient places on the spine, a better outcome is realized for the patient.

The deflection rods of the present invention include in particular embodiments a deflectable post, a spring and a mounting/securing device. The deflectable post and mounting/securing device are typically made of biocompatible metal or metals, e.g. titanium and stainless steel. The spring is made of an elastic material, which may be a polymer or a metal. Suitable polymers include, for example, PEEK and Bionate®. Suitable metals include, for example, titanium, steel and Nitinol. The mounting/securing device secures the deflection rod to an anchoring device, for example, a bone screw, in a manner which allows deflection of the deflectable post. In some embodiments, the deflection rod is integrated with an anchoring device rather than selectably and/or removably mounted.

The deflectable post is configured to connect to the vertical rod system. The deflectable post may deflect relative to the anchoring device by compressing the spring. The deformation of the spring imparts force-deflection characteristics to the deflectable post. The movement of the deflectable post relative to the anchoring device allows controlled movement of the bone anchor (and vertebra in which it is implanted) relative to the vertical rod system. The deflection rod, thus, supports the vertebrae to which the bone anchors are attached while allowing movement of the vertebrae thereby providing for dynamic stabilization of the spine. In a dynamic stabilization assembly incorporating the deflection rod, the load sharing and deflection is provided by the deflection rod and to a lesser degree or not in the vertical rod such as the vertical rod 106 of FIG. 1A.

Deflection rods can be manufactured in a range from stiff configurations to compliant configurations by appropriate selection of the design, materials and dimensions of the post, spring and shield/housing. In particular, the spring rate of the spring can be adjusted to control the stiffness/flexibility of the deflection rod. Deflection rods having a particular stiffness/flexibility may be selected for use in a dynamic stabilization assembly based upon the physiological needs of a particular patient. In a preferred embodiment, deflection rod stiffness/flexibility is selected to provide load sharing in conjunction with from 50% to 100% of the normal range of motion of a patient and more preferably 70% to 100% of the normal range of motion of a patient.

In some cases, certain of the deflection rods of a dynamic stabilization assembly can have a different stiffness or compliance than other of the deflection rods. Thus, in the same assembly, a first deflection rod can have a first flexibility or stiffness or rigidity, and a second deflection rod can have a second different flexibility or stiffness or rigidity depending on the needs of the patient. Particular embodiments of a dynamic stabilization assembly may utilize deflection rods having different deflection properties for each level and/or side of the dynamic stabilization assembly. In other words, one portion of a dynamic stabilization assembly may offer more resistance to movement than the other portion based on the design and selection of different on the deflection rods having different stiffness characteristics, if that configuration benefits the patient.

Figure 2F:
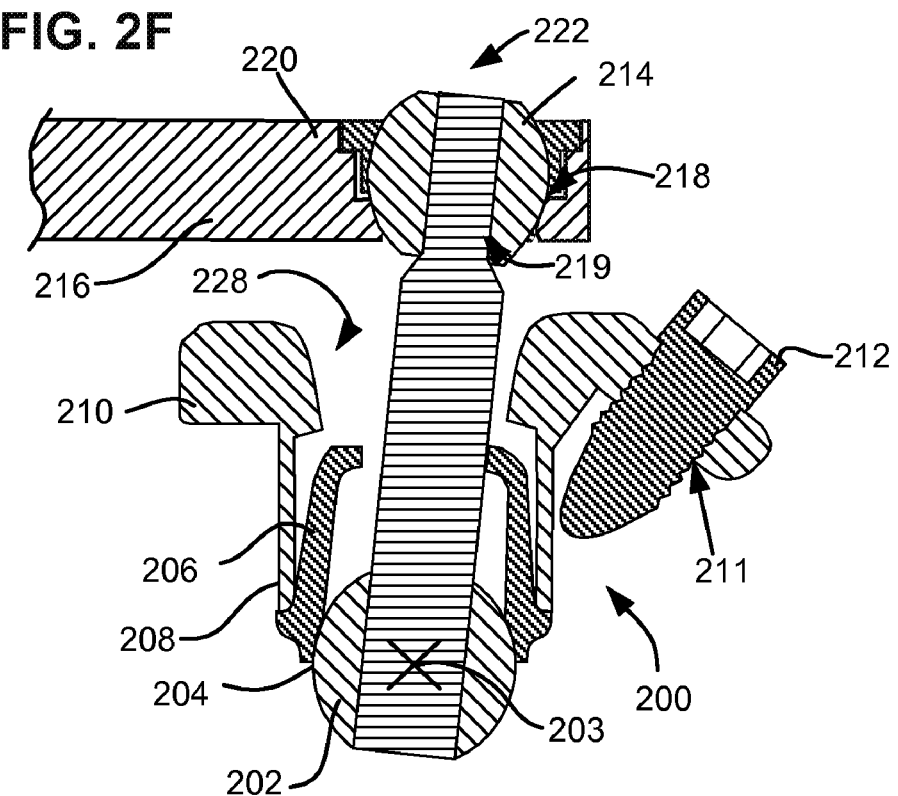
FIGS. 2F and 2G are sectional views of the deflection rod of FIGS. 2A and 2C showing deflection of the post.

FIGS. 2A through 2G illustrate the design and operation of a first embodiment of a deflection rod according to an embodiment of the present invention. FIG. 2A shows an exploded view of deflection rod 200. Deflection rod 200 includes retainer 202, deflectable post 204, spring 206, shield 208, collar 210, screw 212 and ball 214. Deflection rod 200 connects to vertical rod 216 at a ball joint which includes ball 214, pocket 218 and cap 220. Shield 208 and collar 210 are securely attached to each other (or formed in one piece). A threaded aperture 211 passes obliquely through collar 210. Threaded aperture 211 is configured to receive a screw 212. Spring 206 is made of a compliant material which permits movement of deflectable post 204 relative to shield 208.

Retainer 202 may be a ball-shaped retainer 202 as shown. Retainer 202 may be formed in one piece with deflectable post 204 or may be securely attached to deflectable post 204. The retainer 202 may be attached by laser welding, soldering or other bonding technology. For example, retainer 202 in the form of a ball, disk, plate or other shape may be laser welded to the distal end of deflectable post 204. Alternatively, retainer 202 may mechanically engage the deflectable post 204 using, for example, threads. For example, a lock ring, toothed locking washer, cotter pin or other mechanical device can be used to secure deflectable post 204 within shield 208.

FIG. 2B shows an enlarged view of spring 206. As shown in FIG. 2B, spring 206 comprises a ring-shaped base 260 from which extends a plurality of lever arms 262. The lever arms extend upwards from base 260 and extend in towards the central axis of ring-shaped base 260. The lever arms 262 define an aperture 264 which is large enough for the passage of deflectable post 204 (not shown). The material of spring 206 is selected such that the lever arms resist bending away from the position shown. Ring-shaped base 260 also includes rim 205 which is engaged by the lower edge of the shield 208 (See FIG. 2A). In some embodiments, spring 206 may be formed separately from deflection rod 200. For example, deflectable post 204 and spring 206 may be press fit into shield 208. Alternatively or additionally, a biocompatible adhesive may be used to bond the spring 206 to the shield 208.

The stiffness of deflection rod 200 is affected by the spring rate of spring 206. The stiffness of the deflection rod 200 can be changed for example by increasing the spring rate of spring 206 and conversely, the stiffness may be reduced by decreasing the spring rate of spring 206. The spring rate of the spring 206 can be, for example, increased by increasing the thickness of the lever arms 262 and/or decreasing the length of the lever arms 262. Alternatively and/or additionally changing the materials of the spring 206 can also affect the spring rate. For example, making spring 206 out of stiffer material increases the spring rate and thus reduces deflection of deflectable post 204 for the same amount of load—all other factors being equal. Spring 206 is preferably made of a biocompatible polymer or metal. Spring 206 may, for example, be made from PEEK, Bionate®, Nitinol, steel and/or titanium.

Spring 206 may have the same spring rate in each direction of deflection of the deflectable post (isotropic). The spring 206 may have different spring rates in different directions of deflection of the deflectable post (anisotropic). For example, the spring 206 can be designed to have a different spring rate in different directions by adjusting, for example, the length, thickness and/or material of the lever arms 262 in one direction compared to another direction. A deflection rod 200 incorporating an anisotropic spring would have different force-deflection characteristics imparted to it by the spring 206 in different directions.

The stiffness of the deflection rod 200 is also affected by factors beyond the spring rate of spring 206. By changing the dimensions and or geometry of the deflectable post 204, spring 206 and the shield 208, the deflection characteristics of the deflection rod 200 can be changed. For example, the stiffness of the deflection rod 200 can be increased by increasing the distance from the pivot point of the deflectable post 204 to the point of contact between the lever arms 262 surrounding aperture 264 and the deflectable post 204. Conversely, the stiffness of the deflection rod 200 can be decreased by decreasing the distance from the pivot point of the deflectable post 204 to the point of contact between the lever arms 262 surrounding aperture 264 and the deflectable post 204.

The stiffness of the deflection rod may thus be varied or customized according to the needs of a patient by controlling the material and design of spring 206 and defection rod 200. The deflection characteristics of the deflection rod 200 can be configured to approach the natural dynamic motion of the spine, while giving dynamic support to the spine in that region. It is contemplated, for example, that the deflection rod can replicate a 70% range of motion and flexibility of the natural intact spine, a 50% range of motion and flexibility of the natural intact spine and a 30% range of motion and flexibility of the natural intact spine.

One feature of the present invention is to allow the efficient manufacture of a range of deflection rods having a range of different force-deflection characteristics. This can readily be accomplished by manufacturing a range of springs having different force-deflection characteristics and leaving the remainder of the components unchanged. In this way, a range of deflection rods may be manufactured with a small number of unique parts. In some cases, a kit is provided to a doctor having a set of deflection rods with different force-deflection characteristics from which the doctor may select the deflection rods most suitable for a particular patient. In other cases, the surgeon may select deflection rods prior to the procedure based upon pre-operative assessment.

Referring now to FIG. 2C, which shows a perspective view of a fully assembled deflection rod 200. When assembled, deflectable post 204 is positioned within spring 206 which is positioned within shield 208. A rim 205 on the outside surface of spring 206 is engaged by the lower edge of the shield 208. Ball-shaped retainer 202 is received in a partially spherical pocket 207 (See FIG. 2D) in the lower edge of spring 206. Deflectable post 204 may thus pivot in any direction about the center of ball-shaped retainer 202 as shown by arrows 230. (The lower half of ball-shaped retainer 202 is adapted to be received in a hemispherical pocket of the bone anchor (See FIG. 2D). The deflectable post 204 can also rotate about the longitudinal axis of the post and the bone anchor as shown by arrow 232.

Referring again to FIG. 2C, ball 214 is connected to the proximal end of deflectable post 204 to provide a component of a ball joint for connecting deflection rod 200 to a vertical rod 216. Ball 214 may be formed in one piece with deflectable post 204 or may be securely attached to deflectable post 204 using a joint, for example, a threaded joint, welded joint or adhesive joint. Retainer 202 is attached to the distal end of deflectable post 204 to prevent deflectable post 204 from being pulled out of spring 206. A cap 220 secures ball 214 within the pocket of vertical rod 216 creating a ball joint 222 which allows vertical rod 216 to rotate 360 degrees around the axis of deflectable post 204 (as shown by arrow 234) and also tilt away from the plane perpendicular to the axis of deflectable post 204 (as shown by arrow 236). Thus, the vertical rod 216 is allowed to rotate and/or have tilting and/or swiveling movements about a center which corresponds with the center of the ball 214 of ball joint 222.

FIG. 2D shows a sectional view of deflection rod 200 through the longitudinal axis. As shown in FIG. 2D spring 206 occupies the space between deflectable post 204 and shield 208 and is deformed by deflection of deflectable post 204 towards shield 208 in any direction. Spring 206 applies force to the deflectable post 204 to push deflectable post 204 towards the center position. FIG. 2D also shows how deflection rod 200 is mounted within the housing 130 of a bone anchor 102. Deflectable post is held in a position substantially coaxial or collinear with bone anchor 102. Note that the bottom end of cavity 132 of housing 130 forms a hemispherical pocket which receives the distal end of retainer 202. Retainer 202 is thus trapped between spring 206 and housing 130 in a ball-joint that allows deflectable post 204 to pivot and rotate relative to bone anchor 102.

FIG. 2D, also illustrates the internal detail of the ball joint 222 which connects vertical rod 216 and deflectable post 204 of deflection rod 200. The lower end of spring 206 includes spherical pocket 218 at one end. The proximal end of the deflectable post 204 is passed through aperture 219 in disk-shaped pocket 218 of the vertical rod 216. The diameter of deflectable post 204 is smaller than the diameter of the aperture 219. Once the proximal end of deflectable post 204 is passed through the aperture 219, ball 214 is attached to deflectable post 204 using threading, fusing, gluing, press fit and/or laser welding techniques, for example. The diameter of the aperture 219 is less than the diameter of the ball 214 to prevent the ball 214 from passing back through the aperture 219. Once the ball 214 is positioned within the disk-shaped pocket 218 of the vertical rod 216, cap 220 is threaded, fused, glued, press fit and/or laser welded, for example, into pocket 218 thereby securing ball 214 within disk shaped pocket 218.

FIG. 2E shows a partial sectional view of a fully assembled deflection rod 200 along the axis indicated by line 2E-2E of FIG. 2C. As shown in FIG. 2E, spring 206 occupies the space between deflectable post 204 and shield 208 and is deformed by deflection of deflectable post 204 towards shield 208 in any direction. Spring 206 resists deflection of deflectable post 204 outwardly from a position that is collinear with the longitudinal axis of the spring 206. Spring 206 may be described for example as a centering spring. The spring rate of spring 206 is selected to generate the desired deflection/load characteristics for the deflection rod.

Figure 2G:
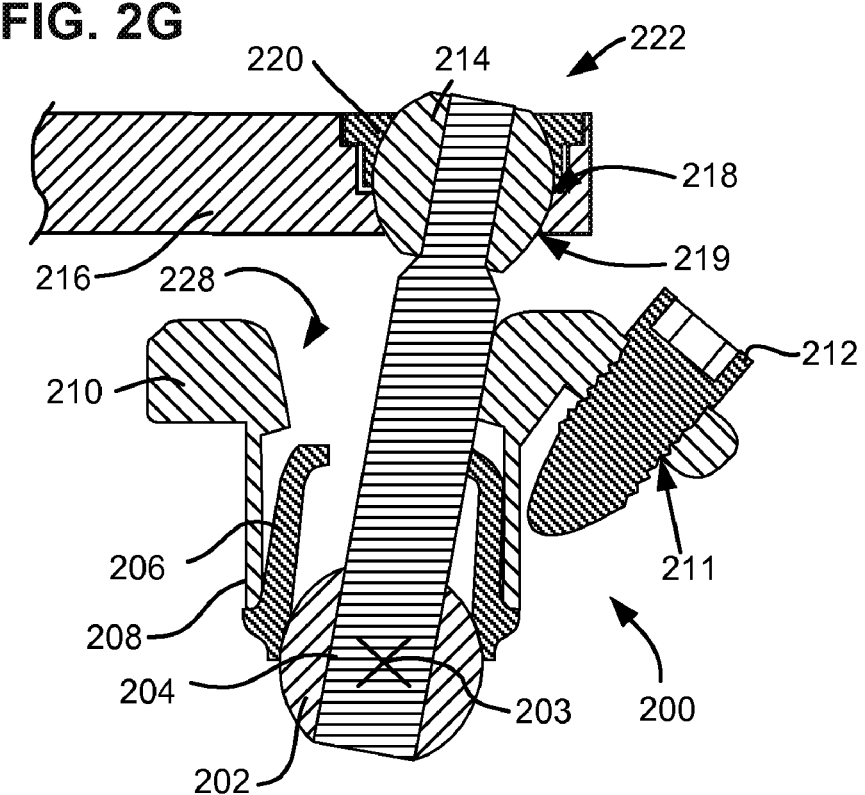

FIGS. 2F and 2G illustrate deflection of deflectable post 204. Applying a force to ball-joint 222 causes deflection of deflectable post 204 relative to shield 208 (and any bone anchor to which it may be mounted). Initially deflectable post 204 pivots about a pivot point 203 indicated by an X. In this embodiment, pivot point 203 is located at the center of ball-shaped retainer 202. In other embodiments, however, pivot point 203 may be positioned at a different location. For example, for other retainer shapes disclosed in the applications incorporated by reference herein, the retainer may pivot about a point which is at the edge of the retainer or even external to the retainer. As shown in FIG. 2F, deflection of deflectable post 204 deforms the spring 206. The force required to deflect deflectable post 204 depends upon the dimensions of deflectable post 204, spring 206 and shield 208 as well as the attributes of the material of spring 206. In particular, the spring rate of spring 206 and elements thereof (See FIG. 2B) may be adjusted to impart the desired force-deflection characteristics to deflectable post 204.

As shown in FIG. 2G, after further deflection, deflectable post 204 comes into contact with limit surface 228 of shield 208. Limit surface 228 is oriented such that when deflectable post 204 makes contact with limit surface 228, the contact is distributed over an area to reduce stress on deflectable post 204 and limit surface 228. As depicted, the limit surface 228 is configured such that as the deflectable post 204 deflects into contact with the limit surface 228, the limit surface 228 is aligned/flat relative to the deflectable post 204 in order to present a larger surface to absorb any load an also to reduce stress or damage on the deflectable. Additional deflection may cause elastic deformation of deflectable post 204. Because deflectable post 204 is relatively stiff, the force required to deflect deflectable post 204 increases significantly after contact of deflectable post 204 with shield 208. For example, the stiffness may double upon contact of the deflectable post 204 with the limit surface 228. In a preferred embodiment, the proximal end of deflectable post 204 may deflect from 0.5 mm to 2 mm before making contact with limit surface 228. More preferably, deflectable post 204 may deflect approximately 1 mm before making contact with limit surface 228.

Thus, as load or force is first applied to the deflection rod by the spine, the deflection of the deflection rod responds about linearly to the increase in the load during the phase when deflection of deflectable post 204 causes compression of spring 206 as shown in FIG. 2F. After about 1 mm of deflection, when deflectable post 204 contacts limit surface 228 (as shown in FIG. 2G) the deflection rod becomes stiffer. Thereafter, a greater amount of load or force needs to be placed on the deflection rod in order to obtain the same incremental amount of deflection that was realized prior to this point because further deflection requires bending of deflectable post 204. Accordingly, the deflection rod provides a range of motion where the load supported increases about linearly as the deflection increases and then with increased deflection the load supported increases more rapidly in order to provide stabilization. Put another way, the deflection rod becomes stiffer or less compliant as the deflection/load increases.

Alternative Deflection Rods/Loading Rods

FIGS. 3A-3D illustrate an alternative deflection rod 300. FIG. 3A shows an exploded view of alternative deflection rod 300. Deflection rod 300 includes ball-shaped retainer 302, deflectable post 304, spring 306, shield 308 and collar 310. In this embodiment, shield 308 and collar 310 are formed in one piece; however, they may be separate components. A mount 314 is present at the proximal end of deflectable post 304 suitable for connecting to a vertical rod. A ball may be used in place of mount 314 as previously described. In this embodiment, mount 314 is formed in one piece with deflectable post 304 and spherical retainer 302. In alternative embodiments, deflectable post 304 may be formed separately from and securely attached to one or more of mount 314 and retainer 302 by laser welding, soldering or other bonding technology. Alternatively, deflectable post 304 may be formed separately and mechanically engage one or more of mount 314 and retainer 302 using, for example, threads. For example, a lock ring, toothed locking washer, cotter pin or other mechanical device can be used to secure deflectable post 304 to one or more of mount 314 and retainer 302.

Spring 306 is made of an elastic material which permits movement of deflectable post 304 relative to shield 308. The spring 306 effectively controls and limits the deflection of the deflectable post 304. Spring 306 is preferably made of a polymer or a metal. For example, spring 306 may be made of Bionate®, PEEK, Nitinol, steel or titanium. The properties of the material and dimensions of spring 306 are selected to achieve the desired spring rate of spring 306 and impart the desired force-deflection characteristics to deflectable post 304. In a preferred embodiment, spring 306 and may be elastically deformed over a range of 0.5-2 mm by deflection of the deflectable post. Spring 306 fits inside shield 308 surrounding deflectable post 304. Spring 306 may be of the same design as spring 206 of FIG. 2B.

In this embodiment, deflection rod 300 is configured to be assembled with a bone anchor 320 prior to implantation of the bone anchor into a vertebra. Bone anchor 320 comprises a threaded bone screw 322 connected to a housing 330. The threads of bone screw 322 are designed to secure bone anchor 320 to a vertebra and may vary in configuration to be adapted to engage particular regions of a vertebra having greater or lesser bone density. Alternative bone anchor configurations are illustrated in FIGS. 8A-8E.

Housing 330 has a cavity 332 oriented along the axis of bone anchor 320 at the proximal end and configured to receive deflection rod 300. Housing 330 also has an outer surface 334 adapted for mounting a component, e.g. an offset connector. Housing 330 may in some embodiments be cylindrical as previously described. As shown in FIG. 3A, outer surface 334 of housing 330 may be provided with flutes 336 or other tool engagement features. Flutes 336 may be engaged by a driver that mates with flutes 336 for implanting and/or removing bone anchor 320.

Referring now to FIG. 3B, which shows a perspective view of a deflection rod 300 assembled with a bone anchor 320. When assembled, deflectable post 304 is positioned within spring 306 of FIG. 3A; spring 306 is positioned within shield 308 of FIG. 3A. Deflectable post 304, spring 306 and shield 308 are then placed in the cavity 332 of bone anchor 320. Threaded collar 310 is then secured in the threaded proximal end of cavity 332. Threaded collar 310 has two sockets 311 for receiving the pins of a pin wrench to allow threaded collar 310 to be tightened to threads 338 of housing 330. Threaded collar 310 is laser welded to housing 330 after installation to further secure the components. Threaded collar 310 secures deflectable post 304, spring 306 and shield 308 within cavity 332 of bone anchor 320. As shown again in FIG. 3B, outer surface 334 of housing 330 may be provided with flutes 336 or other tool engagement features. Flutes 336 may be engaged by a driver that mates with flutes 336 for implanting and/or removing bone anchor 320.

FIG. 3C illustrates the head of an open wrench 380 for driving bone anchor 320 into position. As shown in FIG. 3D, deflection rod 300 is already assembled with bone anchor 320 and thus a driver may not be inserted in the cavity of bone anchor 320. Open wrench 380 has a head 382 designed to engage the exterior surface 334 of housing 330. Exterior surface 334 is provided with features such as flutes 336 to facilitate engagement of housing 330 by open wrench 380. With such a tool, the housing 330 can be engaged and rotated about the longitudinal axis of the bone anchor 320 in order to drive the bone anchor into the bone. Open wrench 380 may be provided with a torque limiting or torque measuring component to facilitate installation of bone anchor 320. In alternative embodiments, a socket, wrench, pin wrench or the like may be used to engage housing 330 in place of an open wrench. In an alternative embodiment, a channel may be made through the long axis of deflectable post 304 communicating (when aligned) with a polygonal channel penetrating into the base of bone anchor 320; an Allen wrench (or similar driver) then may be passed through the deflectable post 304 to engage the bone anchor 320 and drive the bone anchor 320 into the bone.

FIG. 3D shows a sectional view of deflection rod 300 as assembled with bone anchor 320 along the line 3D-3D of FIG. 3B. Ball-shaped retainer 302 is received in a hemispherical pocket 333 in the bottom of cavity 332. The bottom edge of spring 306 secures ball-shaped retainer 302 within hemispherical pocket 333 forming a ball-joint which allows post 304 to pivot and rotate around the center of ball-shaped retainer 302. Spring 306 is held in place by shield 308 which is secured to housing 330 by threaded collar 310.

When assembled, deflectable post 304 may pivot about the center of ball-shaped retainer 302. As shown in FIG. 3D spring 306 occupies the space between deflectable post 304 and shield 308 and is deformed by deflection of deflectable post 304 towards shield 308 in any direction. Spring 306 applies force to deflectable post 304 to push deflectable post 304 towards the center position. The force is applied by spring 306 to deflectable post 304 is dependent upon the spring rate of spring 306 and the amount of deflection. Spring 306 is designed and/or selected to impart the desired force-deflection characteristics to deflectable post 304.

After deflectable post 304 has deflected a certain amount, deflectable post 304 contacts the limit surface 328 of collar 310. Thereafter, further deflection of mount 314 requires bending of deflectable post 304. In this region then, spring 306 and deflectable post 304 both contribute to the desired force-deflection characteristics of deflection rod 300. Because deflectable post 304 is relatively stiff, the deflection rod 300 becomes substantially stiffer after contact between deflectable post 304 and limit surface 328. Put another way, the amount of deflection of mount 314 per additional unit of load decreases after contact between deflectable post 304 and limit surface 328. In a preferred embodiment, the stiffness of deflection rod 300 is increased by two times or more upon contact between deflectable post 304 and limit surface 328. Accordingly, the deflection rod provides a range of motion where the load supported increases about linearly as the deflection increases and then with increased deflection the load supported increases more rapidly in order to provide stabilization.

Figure 4C:
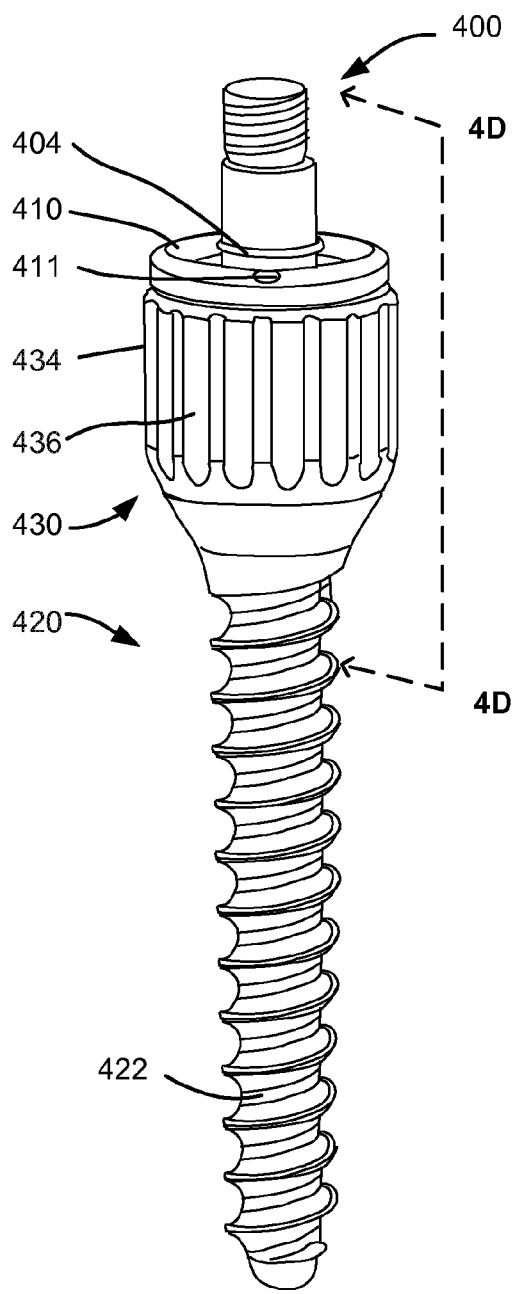
FIG. 4C is a perspective view of the deflection rod of FIG. 4A, as assembled.

FIGS. 4A-4D illustrate an alternative deflection rod 400. FIG. 4A shows an exploded view of alternative deflection rod 400. Deflection rod 400 includes ball-shaped retainer 402, deflectable post 404, spring 406, shield 408 and collar 410. In this embodiment, shield 408 and collar 410 are formed as separate components. A mount 414 is present at the proximal end of deflectable post 404 suitable for connecting to a vertical rod. A ball may be used in place of mount 414 as previously described. In this embodiment, mount 414 is formed in one piece with deflectable post 404 and retainer 402. In alternative embodiments, deflectable post 404 may be formed separately from and securely attached to one or more of mount 414 and retainer 402 by laser welding, soldering or other bonding technology. Alternatively, deflectable post 404 may be formed separately and mechanically engage one or more of mount 414 and retainer 402 using, for example, threads. For example, a lock ring, toothed locking washer, cotter pin or other mechanical device can be used to secure deflectable post 404 to one or more of mount 414 and retainer 402.

Spring 406 is made of an elastic material which permits movement of deflectable post 404 relative to shield 408. The spring 406 effectively controls and limits the deflection of the deflectable post 404. Spring 406 is preferably made of a polymer or a metal for example, PEEK, Bionate®, titanium, steel or Nitinol. The spring rate of spring 406 is selected to achieve the desired force-deflection characteristics for deflectable post 404. The design, dimensions and material of spring 406 are selected to achieve the desired spring rate. In one preferred embodiment, spring 406 is made of PEEK and may be elastically deformed to allow from about 0.5 mm to 2 mm of travel in either direction by mount 414. Spring 406 fits inside shield 408 surrounding deflectable post 404. Spring 406 could be replaced with a spring similar to spring 206 of FIG. 2B.

In this embodiment, deflection rod 400 is configured to be assembled with a bone anchor 420 prior to implantation of the bone anchor. Bone anchor 420 comprises a threaded bone screw 422 connected to a housing 430. The threads of bone screw 422 are designed to secure bone anchor 420 to a vertebra and may vary in configuration so as to be adapted to engage particular regions of a vertebra having greater or lesser bone density.

Housing 430 of bone anchor 420 has a cavity 432 oriented along the axis of bone anchor 420 at the proximal end and configured to receive deflection rod 400. Housing 430 also has an outer surface 434 adapted for mounting a component, e.g. an offset connector. Housing 430 may, in some embodiments, be cylindrical as previously described. As shown in FIG. 4A, outer surface 434 of housing 430 may be provided with flutes 436 or other tool engagement features. Flutes 436 may be engaged by a driver that mates with flutes 436 for implanting and/or removing bone anchor 420.

FIG. 4B shows an enlarged view of spring 406. As shown in FIG. 4B, spring 406 comprises a plurality of spring elements 460. Each spring element 460 is in the form of a leaf spring. Each spring element 460 has a first end 462 and a second end 463 shaped to engage the shield and maintain the orientation of the spring elements 460. Between the first end 462 and second end 463, the spring elements curve in towards a raised middle section 464 which is designed to engage the deflectable post 404 (see FIG. 4A). When the plurality of spring elements 460 is assembled, the middle sections 464 define an aperture 465 sized to receive the deflectable post 404. When assembled with deflectable post 404, movement of flexible post 404 pushes on middle section 464 of one or more spring element 460 causing the one or more spring elements 460 to flatten out. The spring elements resist this deformation and apply a restoring force to the deflection rod 404 to cause it to return to the center position. The force applied to deflectable post 404 is dependent upon the spring rate of spring 406 and the amount of deflection of deflectable post 404.

Spring elements 460 may be individual elements as shown, or they may be joined together, for example at the first ends 462 and/or second ends 463. If joined together, spring elements 460 may all be connected, or may be connected in two parts such that the two parts may be assembled from either side of deflectable post 404 during assembly with shield 408. Spring elements 460 may, in some embodiments, be formed in one piece, for example, machined or molded from a single block of material. In other embodiments, spring elements 460 may be formed as separate pieces and then attached to one another.

The spring rate of each spring element 460 may be controlled during design by choice of the design, dimensions and material of the spring element 460. For example, making the material of the spring elements 460 thicker or reducing the length of the spring element 460 can increase the spring rate of the spring element. Also, the material of the spring element 460 may be selected to achieve the desired force-deflection characteristics. The spring elements 460 may be identical thereby resulting in a force-deflection curve that is substantially uniform in all directions (isotropic). In other embodiments, the spring elements may have different spring rates thereby allowing the force-deflection curve of the deflection rod to be anisotropic—i.e. the deflection of delectable post 404 has different force-deflection characteristics in different directions.

Referring now to FIG. 4C, which shows a perspective view of a deflection rod 400 assembled with a bone anchor 420. When assembled, deflectable post 404 is positioned within spring 406 of FIG. 4A; spring 406 is positioned within shield 408 of FIG. 4A. Deflectable post 404, spring 406 and shield 408 are then placed in the cavity 432 of bone anchor 420. Threaded collar 410 is then secured in the threaded proximal end of cavity 432. Threaded collar 410 has two sockets 411 for receiving the pins of a pin wrench to allow threaded collar 410 to be tightened to threads 438 of housing 430. Threaded collar 410 is laser welded to housing 430 after installation to further secure the components. Threaded collar 410 secures deflectable post 404, spring 406 and shield 408 within cavity 432 of bone anchor 420.

Figure 4D:
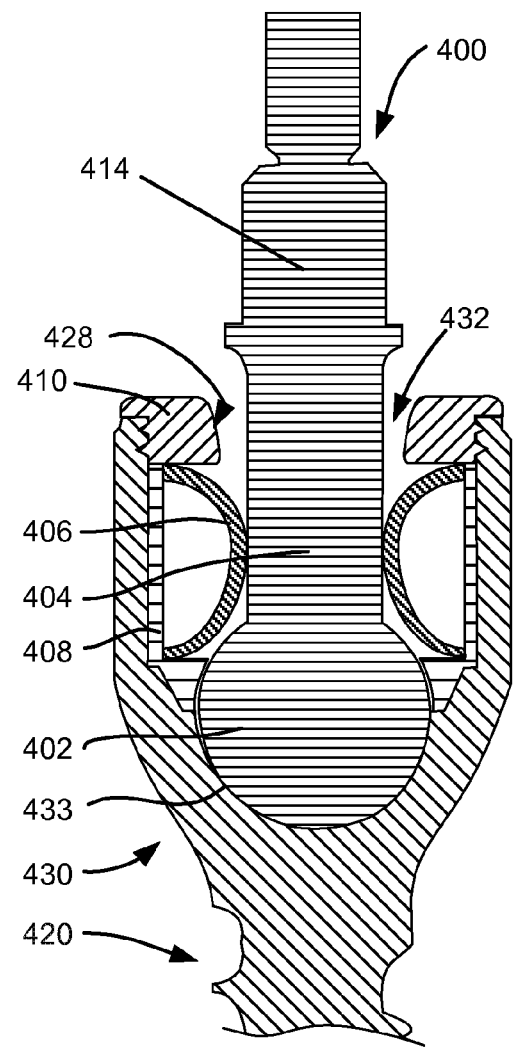
FIG. 4D is a sectional view of the deflection rod of FIG. 4A, as assembled.

FIG. 4D shows a sectional view of deflection rod 400 as assembled with bone anchor 420 along the line 4D-4D of FIG. 4C. Ball-shaped retainer 402 is received in a hemispherical pocket 433 in the bottom of cavity 432. In this embodiment, the bottom edge of sleeve 408 secures ball-shaped retainer 402 within hemispherical pocket 433 forming a ball-joint which allows post 404 to pivot and rotate around the center of ball-shaped retainer 402. Shield 408 is held in position by collar 410 thereby securing retainer 402. Spring 406 is also secured by collar 410 between collar 410 and the bottom end of shield 408.

When assembled, deflectable post 404 may pivot about the center of ball-shaped retainer 402. Deflectable post 404 may also rotate about the long axis of the post. As shown in FIG. 4D, spring 406 occupies the space between deflectable post 404 and shield 408 and is deformed by deflection of deflectable post 404 towards shield 408 in any direction. Spring 406 applies force to the deflectable post 404 to push deflectable post 404 towards the center position. The force applied by spring 406 to deflectable post 404 depends upon the spring rate of spring 406 and the amount of deflection. Thus spring 406 imparts the desired force-deflection characteristics to the deflectable post 404.

After deflectable post has deflected a certain amount, deflectable post 404 contacts the limit surface 428 of collar 410. Thereafter, further deflection of mount 414 requires bending of deflectable post 404. In this region the, both spring 406 and deflectable post 404 contribute to the desired force-deflection characteristics of deflection rod 400. Because deflectable post 404 is relatively stiff, the deflection rod becomes substantially stiffer after contact between deflectable post 404 and limit surface 428. Put another way, the amount of deflection of mount 414 per additional unit of load decreases after contact between deflectable post 404 and limit surface 428. In a preferred embodiment, the stiffness of deflection rod 400 is increased by two times or more upon contact between deflectable post 404 and limit surface 428. Accordingly, the deflection rod provides a range of motion where the load supported increases about linearly as the deflection increases and then with increased deflection the load supported increases more rapidly in order to provide stabilization.

FIGS. 5A-5C show another alternative deflection rod having a different mechanism to secure the deflectable post to the deflection rod and/or the bone anchor and a different spring mechanism. The mechanisms of FIGS. 5A-5B may be adapted for use in other of the deflection rods described herein.

FIG. 5A shows an exploded view of alternative deflection rod 500. Deflection rod 500 includes ball-shaped retainer 502, post 504, spring 506, split-ring 538, collar 510, and mount 514. In this embodiment, ball-shaped retainer 502 is formed in one piece with post 504. In this embodiment deflection rod 500 is assembled with a bone anchor 520, which comprises a bone screw 522 connected to a housing 530. Housing 530 has a cavity 532 oriented along the axis of bone anchor 520 and configured to receive deflection rod 500. Housing 530 also has an outer surface adapted for mounting a component, e.g. an offset connector. As shown in FIG. 5A, the outer surface of housing 530 is provided with flutes 531. Flutes 531 may be engaged by, e.g. an offset connector and/or a driver for implanting bone anchor 520.

In this embodiment, retainer 502 is a ball-shaped retainer. Mount 514 is suitable for connecting to a vertical rod. A second ball may be used in place of mount 514 as previously described. In this embodiment, mount 514 is formed in one piece with deflectable post 504. In a preferred embodiment, mount 514, ball-shaped retainer 502 and deflectable post 504 are formed from a single piece of titanium. In alternative embodiments, deflectable post 504 may be formed separately from, and securely attached to, one or more of mount 514 and retainer 502 by laser welding, soldering or other bonding technology. Alternatively, deflectable post 504 may be formed separately and mechanically engage one or more of mount 514 and retainer 502 using, for example, threads, a lock ring, toothed locking washer, cotter pin or other mechanism.

Spring 506 fits inside cavity 532 of housing 530 surrounding post 504. Spring 506 is inserted in cavity 532 of housing 530 over post 504. Threaded collar 510 is then secured in the threaded proximal end of cavity 532. Threaded collar 510 has two sockets 511 for receiving the pins of a pin wrench to allow threaded collar 510 to be tightened to housing 530. Threaded collar 510 is laser welded to housing 530 after installation to further secure the components. Threaded collar 510 secures spring 506 within cavity 532 of bone anchor 520.

FIG. 5B shows a sectional view of a deflection rod 500 assembled with a bone anchor 520. Ball-shaped retainer 502 may be locked in a ball-joint pocket in a variety of ways. Some suitable methods and devices for locking a ball in a ball-joint assembly are disclosed in U.S. Pat. No. 4,666,330 titled "Ball Joint Assembly" to O'Connell et al. which is incorporated herein by reference in its entirety. As shown in FIG. 5B, ball-shaped retainer 502 fits in pocket 534 in the bottom of cavity 532 of housing 530. Pocket 534 is generally hemispherical. The entrance aperture 535 to pocket 534 is the same diameter as ball-shaped retainer 502. However, entrance aperture 535 includes a groove 533 which receives a split-ring 538. Split-ring 538 has a larger diameter than aperture 535 but split-ring 538 is compressed slightly during installation. After passing through aperture 535, split-ring 538 expands outwards to occupy groove 533. Split-ring 538, when positioned in groove 533, reduces the effective diameter of aperture 535 and thereby prevents removal of ball-shaped retainer 502. Other shapes of retainer and pocket may also be used as long as they pivotally secure the post 504 to the bone anchor 520 and allow the desired range of travel for post 504. In the deflection rod 500 of FIG. 5A-5B, no shield is needed between spring 506 and housing 530. By removing the thickness of the shield, the size/strength properties of the device may be enhanced.

When assembled, deflectable post 504 may pivot about the center of ball-shaped retainer 502. As shown in FIG. 5B, spring 506 occupies the space between post 504 and housing 530. Spring 506 is compressed by deflection of post 504 towards housing 530 in any direction. Spring 506 applies force to the deflectable post 504 to push deflectable post 504 towards the center position. The force applied by spring 506 to deflectable post 504 is dependent upon the spring rate of spring 506 and the amount of deflection of deflectable post 504. Thus, spring 506 initially imparts the desired force-deflection characteristics to post 504.

The interior surface of cavity 532 of housing 530 and/or collar 510 is shaped to provide the limit surface 572 to limit deflection of post 504. In a preferred embodiment, the spring may be compressed about 1 mm by deflection of the post 504 prior to contact of post 504 with limit surface 572 of collar 510. Thereafter, further deflection of mount 514 necessitates bending of post 504 and/or bone anchor 520. Post 504 and anchor 520 are stiffer than spring 506, thus upon contact of post 504 and limit surface 572, further deflection requires greater force per unit of deflection than prior to such contact. In preferred embodiments, the stiffness of the system increases to about double the stiffness of the spring after contact is made between post 504 and limit surface 572.

In this embodiment, spring 506 is formed from a plurality of planar springs 560. Spring 506 may comprise one or more planar springs 560. Planar springs 560 may be cut or stamped from a flat sheet of material. Spring 506 is preferably made of a biocompatible elastic polymer or metal. For example, planar springs 560 may be made from, Bionate®, Peek, Nitinol, steel and/or titanium. The properties of the design, dimensions and material of the spring 506 and deflectable post 504 are selected to achieve the desired force-deflection characteristics for deflectable post 504. In some embodiments, the number of planar springs 560 in a particular deflection rod may be selectable such that stiffer deflection rods have a larger number of planar springs 560 and more compliant deflection rods have a lower number of planar springs 560. In other embodiments, the spring rate of each spring 506 may be adjusted by design, dimension or material changes.

FIG. 5C shows an enlarged view of one possible embodiment of a planar spring 560. As shown in FIG. 5C, planar spring 560 comprises an inner ring 564 connected to an outer ring 562 by a plurality of oblique lever arms 566. Outer ring 562 is sized to fit within cavity 532 of FIG. 5A. Inner ring 564 is sized so that aperture 565 just fits over post 504. The arrangement of lever arms 566 allows inner ring 564 to deflect laterally with respect to outer ring 562 by deforming lever arms 566. The lever arms resist the deformation. When assembled with post 504 and housing 530 inner ring 564 engages post 504 and outer ring 562 engages housing 530. When deflectable post 504 deflects towards housing 530, lever arms 566 are elastically deformed. Planar spring 560 imparts a return force upon post 504 upon deflectable post 504 pushing it away from housing 530 toward the center (neutral position). The force applied by spring 506 to deflectable post 504 is dependent upon the spring rate of spring 506 and the amount of deflection of deflectable post 504.

The spring/spring elements in the deflection rod of FIGS. 5A-5B are designed to elastically deform in the radial direction (relative to post 504). Alternative designs of springs may be used to control deflection of post 504 including, for example, spring washers, Belleville washers/disc springs, CloverDome™ spring washers, CloverSprings™, conical washers, wave washers, coil springs and finger washers. Examples of alternative springs which may be used in the deflection rod of FIGS. 5A-5B are shown in FIGS. 5D-5G.

FIG. 5D shows an enlarged view of an alternative embodiment of a planar spring 560d. As shown in FIG. 5D, planar spring 560d comprises an inner ring 564d connected to a plurality of oblique lever arms 566d. The outer ends 562d of lever arms 566d are positioned to fit within cavity 532. Inner ring 564d is sized so that aperture 565d just fits over post 504. The arrangement of lever arms 566d allows inner ring 564d to deflect laterally with respect to cavity 532 (FIG. 5B) by deforming lever arms 566d. The lever arms 566d resist the deformation. When assembled with post 504 and housing 530, planar spring 560d imparts a return force upon post 504 upon deflection of post 504 towards housing 530. One or more springs 560d may be used in the deflection rod of FIGS. 5A-5B.

FIG. 5E shows an enlarged view of an alternative embodiment of a spring 560e. As shown in FIG. 5E, spring 560e is a coil spring. The coil spring 560e is wound to form an inner ring 564e and an outer ring 562e. The outer ring 562e is sized to fit within cavity 532 (FIG. 5B). The inner ring 564e is sized so that aperture 565e just fits over post 504. Between inner ring 564e and outer ring 562e, are a plurality of helical coils 566e. The arrangement of coils 566e allows inner ring 564e to deflect laterally with respect to outer ring 562e by deforming coils 566e. The coils 566e resist the deformation. When assembled with post 504 and housing 530, coil spring 560e imparts a return force upon post 504 when post 504 deflects towards housing 530 (FIG. 5B). One or more springs 560e may be used in the deflection rod of FIGS. 5A-5B.

FIGS. 5F and 5G show an enlarged view of an alternative embodiment of a spring 560f. FIG. 5G shows a side view of spring 560f in which it can be seen that spring 560f is a domed spring washer. The domed spring washer 560f has an inner aperture 564f and an outer circumference 562f. The outer circumference 562f is sized to fit within cavity 532 (FIG. 5B). The inner aperture 564f is sized to fit over post 504. Domed spring washer 560f has a plurality of interior and exterior cutouts 566f. These cutouts increase the compliance of domed spring washer 560f (but reduce stiffness). The cutouts are designed to allow the desired degree of lateral deformation while still providing the desired spring rate. The pattern of cutouts shown in FIG. 5F forms a clover pattern but other patterns may be used, for example, fingers. The design of domed spring washer 560f allows inner aperture 564f to deflect laterally with respect to outer circumference 562f by deforming the material of domed spring washer 560f. The material resists the deformation. When assembled with post 504 and housing 530, domed spring washer 560f imparts a return force upon post 504 when post 504 deflects towards housing 530. One or more spring washers 560f may be used in the deflection rod of FIGS. 5A-5B.

Figure 6A:
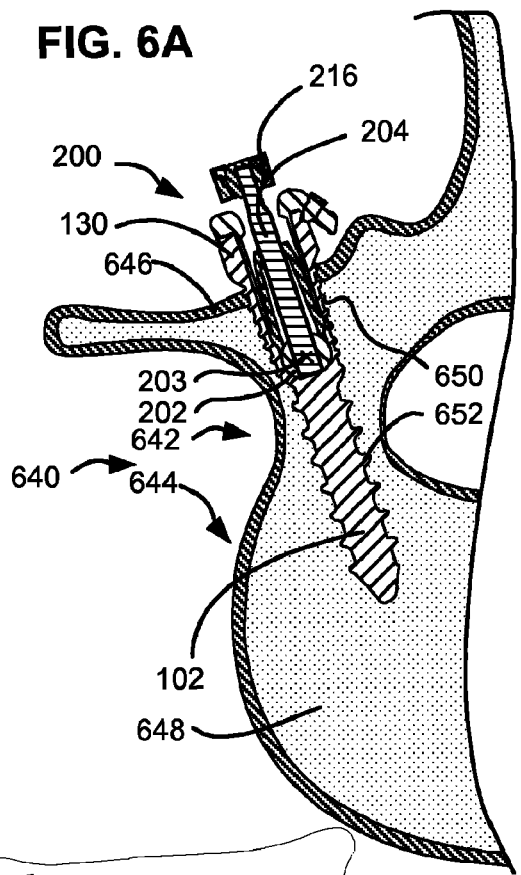
FIG. 6A is a transverse sectional view of a vertebra illustrating the implantation of a deflection rod and bone anchor according to an embodiment of the invention.

FIG. 6A is a sectional view illustrating the implantation of deflection rod 200 of FIG. 2A in a vertebra 640. As shown in FIG. 6A, a bone anchor 102 is oriented such that is passes through pedicle 642 into vertebral body 644 of vertebra 640. Note that the length of bone anchor 102 is selected based upon the anatomy of the patient. Thus, shorter bone anchors are used in smaller vertebrae and longer bone anchors are used in larger vertebrae. As shown in FIG. 6A, bone anchor 102 has shallower threads 650 adjacent housing 130. These shallow threads 650 engage the harder cortical bone 646 on the surface of the vertebra 640. Bone anchor 102 has deeper threads 652 towards the distal end of bone anchor 102. These threads 652 are better suited to engage the softer cancellous bone 648 within the vertebral body 644.

As shown in FIG. 6A deflection rod 200 is mounted within bone anchor 102 such that pivot point 203 is positioned below the surface of vertebra 640. Deflectable post 204 pivots about this pivot point 203 positioned close to or within vertebra 640. This is advantageous in that it places pivot point 203 of deflectable post 204 closer to the vertebral body 644 and thus closer to the natural instantaneous center of rotation of the spine. Placing pivot point 203 closer to the vertebral body 644 promotes natural motion and reduces non-physiological forces on the bones and strain on the system. Placing the pivot point 203 closer to the vertebral body 644 also helps isolate bone anchor 102 from the relative motion between vertebra 640 and the vertical rod 216 which connects one vertebra to another vertebra. Pivot point 203 is preferably close to the surface of the vertebra 640 and more preferably pivot point 203 is within the vertebrae 640. Even more preferably, the pivot point 203 is positioned within the pedicle 642 of the vertebra 640 within the natural range of the instantaneous center of rotation of the spine. Although, in this embodiment, pivot point 203 is positioned at the center of retainer 202, in other embodiments, as described in the applications incorporated by reference herein, the effective pivot point may be located at the edge of the retainer or even outside of the retainer.

Figure 6B:
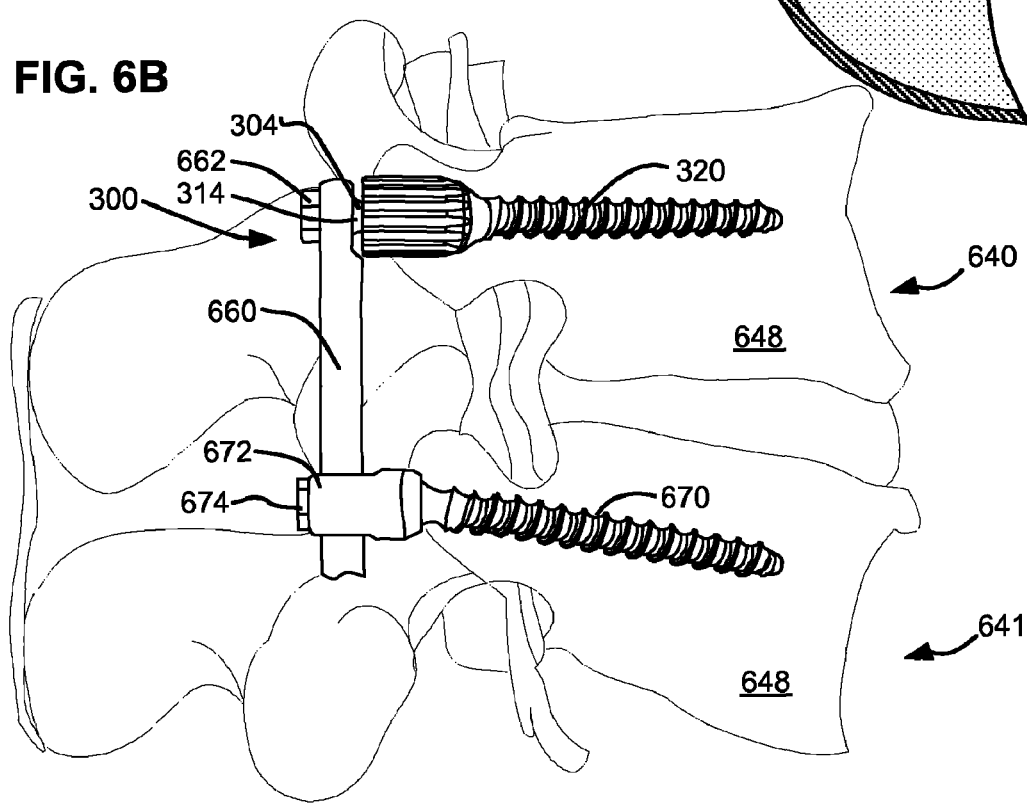
FIG. 6B is a lateral view of the spine illustrating a single level dynamic stabilization system utilizing a deflection rod according to an embodiment of the invention.

FIG. 6B shows a lateral view of a dynamic stabilization assembly utilizing deflection rod 300 of FIG. 3A. As shown in FIG. 6B, deflection rod 300 is installed in bone anchor 320. Bone anchor 320 is implanted in a vertebra 640. A polyaxial screw 670 is implanted in a second vertebra 641. A vertical rod 660 is secured at one end to mount 314 of deflection rod 300. Mount 314 in this embodiment passes through an aperture in vertical rod 660. A threaded nut 662 secures vertical rod 660 directly to mount 314. The rigid connection between vertical rod 660 and deflection rod 300 provides a relatively stiff assembly. However, where greater range of motion/less stiffness is desired, vertical rod 660 may be connected to deflectable post 304 by a ball-joint, for example as previously described with respect to FIGS. 1A-1B.

Vertical rod 660 is mounted at the other end to the polyaxial head 672 of polyaxial screw 670. This screw 670 may be a standard polyaxial screw, for example, a 5.5 mm polyaxial screw available in the marketplace. This screw 670 may, alternatively, be a bone anchor with a polyaxial head e.g. the polyaxial head previously described with respect to FIG. 1C. Alternatively, screw 670 may include a deflection rod and bone anchor as described herein and a suitable connector to mount the deflection rod to the vertical rod 660. In a preferred embodiment, vertical rod 660 is a titanium rod 5.5 mm in diameter as used in rigid spinal implants. The vertical rod 660 is secured to polyaxial head 672 using a threaded fitting, set screw 674, for example. The vertical rod 660 thereby supports the vertebrae while deflection rod 300 provides for load sharing and allows relative motion of vertebra 640 relative to vertebra 641. Thus, the dynamic stabilization assembly provides dynamic stabilization of the spine and load sharing. The dynamic stabilization assembly may be expanded to two or more levels using, for example, an offset connector mounted to the housing 330 of bone anchor 320. Thus, a modular system is provided which provides for the creation of a multi-level dynamic stabilization assembly.

FIGS. 7A and 7B show an alternative embodiment of deflection rod 700 which includes a mount 770 for connecting the deflection rod to a vertical rod. As shown in FIG. 7A, mount 770 includes a circular plate 774; the face of which is parallel to the longitudinal axis of deflectable post 704. A threaded pin 772 projects from the center of circular plate 774. Threaded pin 772 is perpendicular to the longitudinal axis of deflectable post 704. On the face of circular plate 774 surrounding pin 772 are a plurality of radial splines 776.

Mount 770 is designed to mate with vertical rod 780 as also shown in FIG. 7A. Vertical rod 780 has at one end a circular plate 784; the face of which is parallel to the longitudinal axis of vertical rod 780. An aperture 782 passes through the center of circular plate 784 and is sized to receive threaded pin 772. Aperture 782 is perpendicular to the longitudinal axis of vertical rod 780. On the face of circular plate 784 surrounding aperture 782 are a plurality of radial splines 786. The radial splines of vertical rod 780 are designed to mate with and engage the splines 776 of mount 770.

As shown in FIG. 7B, aperture 782 of vertical rod 780 is received over threaded pin 772 of mount 770. The angle of vertical rod 780 relative to deflectable post 704 may be adjusted as shown by arrow 792. Adjustment of the relative angle of deflectable post 704 and vertical rod 780 combined with the ability of deflectable post 704 to rotate about its long axis (as shown by arrow 794) relative to bone anchor 720 provides two degrees of freedom and thus sufficient flexibility of installation to align vertical rod 780 with a bone anchor implanted in another vertebrae. As shown in FIG. 7B, a nut 790 engages threaded pin 772 to secure plate 774 to plate 784. Splines 776 of plate 774 are arranged facing splines 786 of plate 784. When nut 790 is tightened, splines 786 engage splines 776 to prevent rotation of vertical rod 780 about pin 772. Thus, when the nut 790 is tightened, the angle between deflectable post 704 and vertical rod 780 is fixed. The vertical rod mounting mechanism of FIGS. 7A and 7B may be readily applied to any of the deflection rod systems described herein.

Alternative Bone Anchors

Figure 8A:
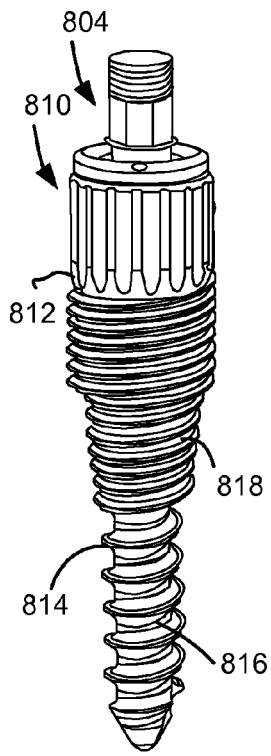
FIGS. 8A-8E are perspective views of alternative combinations of deflection rods and bone anchors according to embodiments of the present invention.

FIGS. 8A though 8E illustrate some possible variations in bone anchors of the anchoring system. The bone anchors each have a housing compatible with the deflection rods of the deflection system and the offset heads/connectors of the connector system. In some embodiments, the deflection rod is installed/assembled in the bone anchor prior to implantation of the bone anchors in the body. In alternative embodiments, the bone anchors may be implanted in the body before installation of a deflection rod.

Bone anchor 810 of FIG. 8A is a bone screw having a threaded region 814 which extends up over most of a housing 812. A deflection rod 804 is installed in housing 812. The threaded region 814 may extend over a greater or lesser amount of housing 812 depending upon such factors as the length of the bone screw, the type of bone in which the screw is to be implanted and the desired height to which the housing 812 will extend above the bone surface after implantation. Bone anchor 810 may be useful to lower the depth of the pivot point of the deflection rod 804 closer to the natural instantaneous center of rotation of the spine. Note also that the distal thread depth 816 may be deeper than the proximal thread depth 818. The distal threads 818 are adapted for engagement of the soft cancellous bone while the proximal threads is adapted for engagement of the harder cortical bone at the surface of the vertebra.

Figure 8B:
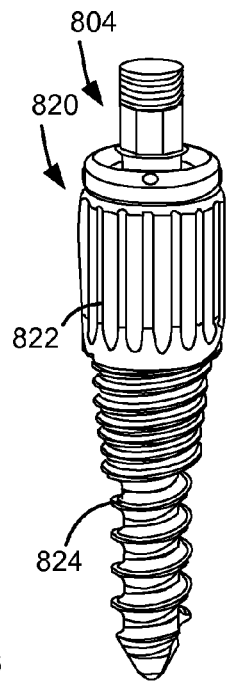

Bone anchor 820 of FIG. 8B is a bone screw in which the screw-only section 824 is shorter in length than in bone screw 810 of FIG. 8A. A deflection rod 804 is installed in housing 822. Different lengths of screw-only section may be useful in different patients or different vertebrae as the size of the bone in which the anchor needs be implanted may vary considerably. For example, short bone screws are desirable where the dynamic stabilization system is to be implanted in smaller vertebrae. The physician may determine the length of bone screw appropriate for a particular patient by taking measurements during the procedure by determining measurements from non-invasive scanning, for example, X-ray NMR, and CT scanning. Note however, that housing 822 is preferably the same size and shape as the housings of the other bone anchors so as to be compatible with the same deflection rods, components and connectors.

Figure 8C:
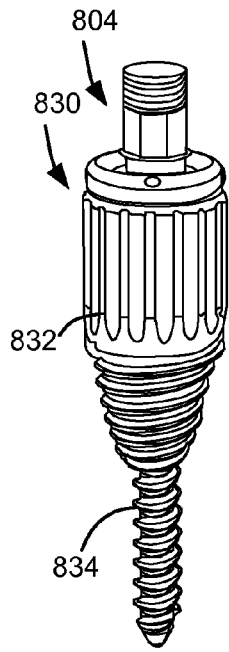

Bone anchor 830 of FIG. 8C is a bone screw in which the screw-only section 834 has a smaller diameter and is shorter in length than in bone screw 810 of FIG. 8A. A deflection rod 804 is installed in housing 832. Different diameters of screw-only section may be useful in different patients or different vertebrae as the size of the bone in which the anchor needs be implanted may vary considerably. For example smaller diameter bone screws may be desirable where the dynamic stabilization system is to be implanted in smaller vertebrae. The physician may determine the diameter of bone screw appropriate for a particular patient by taking measurements during the procedure of by determining measurements from non-invasive scanning, for example, X-ray NMR, and CT scanning. Note however, that housing 832 is preferably the same size and shape as the housings of the other bone anchors so as to be compatible with the same deflection rods, components and connectors.

Figure 8D:
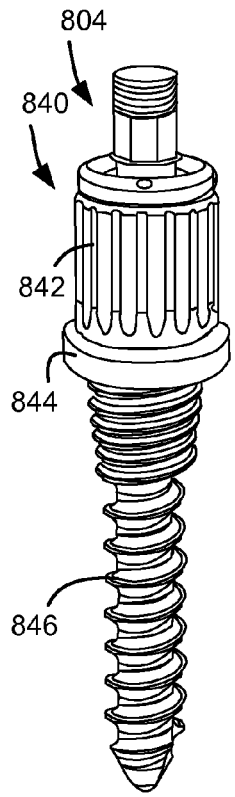

Bone anchor 840 of FIG. 8D is a bone screw in which the housing 842 has a rim 844 extending away from housing 842 where it transitions to the threaded region 846. A deflection rod 804 is installed in housing 842. Rim 844 may serve to retain an offset head mounted to housing 842 in a way that it can rotate freely around housing 842 during installation. Rim 844 may also serve to widen the contact area between the bone anchor 840 where it meets the bone of the vertebra. This can act as a stop preventing over-insertion. This can also provide a wide base for stabilizing the housing against lateral motion and torque. Note that housing 842 is preferably the same size and shape as the housings of the other bone anchors so as to be compatible with the same deflection rods and connectors.

Figure 8E:
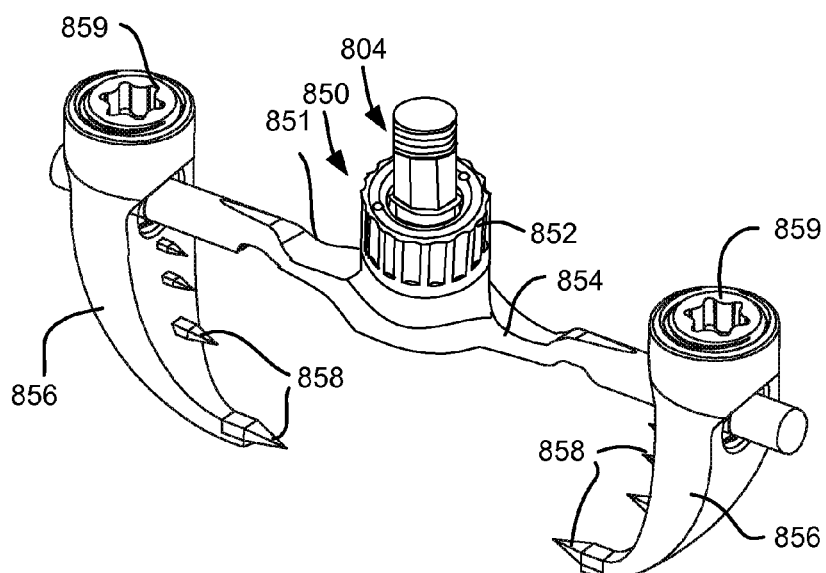

Bone anchor 850 of FIG. 8E illustrates a bone hook device 851 having a housing 852. A deflection rod 804 is installed in housing 852. Bone hook device 851 comprises a bar 854 to which housing 852 is rigidly connected. At either end of bar 854 is a bone hook 856 having a set screw 859 for securing the bone hook 856 to the bar 854. Each bone hook 856 has a plurality of sharp points 858 for engaging and securing the bone hook 856 to a vertebra. During use, the bone hooks 856 are urged towards each other until the sharp points engage and/or penetrate the surface of a bone. Set screws 859 are tightened to secure bone hooks 856 in position relative to bar 854 and thus secure housing 852 relative to the bone. Different arrangements of bone hooks and bars may be made suitable for attachment of the housing 852 to different types, sizes, shapes and locations of vertebra. Note that housing 852 is preferably the same size and shape as the housings of the other bone anchors so as to be compatible with the same deflection rods, components and connectors.

Deflection Rod/Loading Rod Materials

Movement of the deflectable post relative to the bone anchor provides load sharing and dynamic stabilization properties to the dynamic stabilization assembly. As described above, deflection of the deflectable post deforms the material of the spring. The spring applies a restoring force upon the deflectable post; the force being dependent upon the spring rate of the spring and the amount of deflection of the deflectable post. The design, dimensions and the material of the spring may be selected to achieve the desired spring rate. The characteristics of the spring in combination with the dimensions of the other components of the deflection rod interact to generate the force-deflection curve of the deflection rod.

The design, dimensions and materials may be selected to achieve the desired force-deflection characteristics. By changing the dimensions of the deflectable post, spring and spring elements the deflection characteristics of the deflection rod can be changed. The stiffness of components of the deflection rod can be, for example, increased by increasing the diameter of the deflectable post. Additionally, decreasing the diameter of the deflectable post will decrease the stiffness of the deflection rod. Alternatively and/or additionally, changing the materials which comprise the components of the deflection rod can also affect the stiffness and range of motion of the deflection rod. For example, making the spring out of stiffer and/or harder material increases the load necessary to cause a given deflection of the deflection rod.

The deflectable post, bone anchor and vertical rods are preferably made of biocompatible implantable metals. The deflectable post can, for example, be made of, titanium, a shape memory metal for example Nitinol (NiTi) or stainless steel. In preferred embodiments, the deflectable post is made of titanium or cobalt chrome. In preferred embodiments, the bone anchor and vertical rods are also made of titanium; however, other materials, for example, stainless steel may be used instead of or in addition to the titanium components. The ball of the vertical rod may also be made of cobalt chrome for its improved wear characteristics.

The spring can be formed by extrusion, injection, compression molding and/or machining techniques, as would be appreciated by those skilled in the art. In some embodiments, the spring is formed separately. For example, a spring may be cut or machined from a biocompatible polymer and then assembled with the deflectable post and spring such as by being press fit into the shield. Alternatively or additionally, a fastener or biocompatible adhesive may be used to secure the spring to the shield and/or post.

The material of the spring is preferably a biocompatible and implantable polymer or metal having the desired deformation characteristics—elasticity and modulus. The material of the spring should also be able to maintain the desired deformation characteristics. Thus the material of the spring is preferably durable, resistant to oxidation and dimensionally stable under the conditions found in the human body. The spring may, for example be made from a PEEK or a polycarbonate urethane (PCU) such as Bionate® or a surgical steel or titanium or Nitinol. If the spring is comprised of Bionate®, a polycarbonate urethane or other hydrophilic polymer, the spring can also act as a fluid-lubricated bearing for rotation of the deflectable post relative to the longitudinal axis of the deflectable post.

Other polymers or thermoplastics may be used to make the spring including, but not limited to, polyether-etherketone (PEEK), polyphenylsolfone (Radel®), or polyetherimide resin (Ultem®). Other polymers that may be suitable for use in some embodiments, for example, other grades of PEEK, for example 30% glass-filled or 30% carbon filled, provided such materials are cleared for use in implantable devices by the FDA, or other regulatory body. Glass-filled PEEK is known to be ideal for improved strength, stiffness, or stability while carbon filled PEEK is known to enhance the compressive strength and stiffness of PEEK and lower its expansion rate.

Still other suitable biocompatible thermoplastic or thermoplastic polycondensate materials may be suitable, including materials that have good memory, are flexible, and/or deflectable have very low moisture absorption, and good wear and/ or abrasion resistance, can be used without departing from the scope of the invention. These include polyetherketoneketone (PEKK), polyetherketone (PEK), polyetherketoneetherketoneketone (PEKEKK), and polyetheretherketoneketone (PEEKK) and generally, a polyaryletheretherketone. Further, other polyketones can be used as well as other thermoplastics.

Still other polymers that can be used in the spring are disclosed in the following documents, all of which are incorporated herein by reference. These documents include: PCT Publication WO 02/02158 A1, dated Jan. 10, 2002 and entitled Bio-Compatible Polymeric Materials; PCT Publication WO 02/00275 A1, dated Jan. 3, 2002 and entitled Bio-Compatible Polymeric Materials; and PCT Publication WO 02/00270 A1, dated Jan. 3, 2002 and entitled Bio-Compatible Polymeric Materials.

The design, dimensions and materials of the spring are selected in combination with the design of the deflection rod to create a deflection rod having stiffness/deflection characteristics suitable for the needs of a patient. By selecting appropriate spring and spring rate the deflection characteristics of the deflection rod can be configured to approach the natural dynamic motion of the spine of a particular patient, while giving dynamic support to the spine in that region. It is contemplated, for example, that the deflection rod can be made in stiffness that can replicate a 70% range of motion and flexibility of the natural intact spine, a 50% range of motion and flexibility of the natural intact spine and a 30% range of motion and flexibility of the natural intact spine. Note also, as described above, in certain embodiments, a limit surface cause the stiffness of the deflection rod to increase after contact between the deflectable post and the limit surface.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

What is claimed is:

1. A dynamic spine stabilization device comprising:
 a bone anchor having a housing;
 a cavity in the housing coaxial with the bone anchor;
 a deflectable post received in the cavity;
 the deflectable post having a retainer at a distal end and a mount at a proximal end;
 the retainer being secured in a pocket of the cavity of the housing such that the deflectable post may pivot and rotate about a longitudinal axis of the deflectable post; and
 a spring positioned in the cavity of the housing between the post and the housing such that pivoting of the post away from a position in which the longitudinal axis of the post is coaxial with the bone anchor causes compression of the spring and such that the spring applies a force upon the post pushing the post towards a position in which the longitudinal axis of the post is coaxial with the bone anchor.

2. The device of claim 1, wherein said spring is made of a polymer.

3. The device of claim 1, wherein said spring is made of a superelastic metal.

4. The device of claim 1, wherein said spring is radially-compressible.

5. The device of claim 1, wherein said spring comprises a plurality of planar spring elements.

6. The device of claim 5 wherein the spring elements are parallel to the deflectable post.

7. The device of claim 1, wherein said housing has a limit surface which contacts the deflectable post upon deflection of said deflectable post a first amount from the position in which the longitudinal axis of the deflectable post is coaxial with the bone anchor.

8. The device of claim 1, wherein:
 said housing has a limit surface which contacts the deflectable post upon deflection of said deflectable post a first amount from the position in which the longitudinal axis of the deflectable post is coaxial with the bone anchor; and
 wherein further deflection of said deflectable post beyond said first amount requires a larger load per unit of deflection than deflection of said deflectable post up to said first amount.

9. The device of claim 1, wherein:
 said housing has a limit surface which contacts the post upon deflection of said deflectable post a first amount from the position in which the longitudinal axis of the deflectable post is coaxial with the bone anchor; and
 wherein further deflection of said deflectable post beyond said first amount requires at least double the load per unit of deflection than deflection of said deflectable post up to said first amount.

10. The device of claim 1, including a connector and a vertical rod, with the connector connecting the vertical rod to the deflectable post and with the deflection under load occurs in the deflectable post and to a lesser degree in the connection rod.

11. The device of claim 1, wherein said post can pivot about a point in said bone anchor, which point is adapted to be implanted within a vertebra.

12. The device of claim 1, wherein said deflection post can pivot about a point in said bone anchor, which point is adapted to be implanted adjacent a surface of a vertebra.

13. The device of claim 1, wherein said spring has an isotropic deflection profile.

14. The device of claim 1, wherein said spring has an anisotropic deflection profile.

15. The device of claim 1 wherein during deflection the deflectable post first is urged against said spring and then is subsequently urged against a limit surface of said housing.

16. A spine stabilization device comprising:
 a bone screw having a distal end adapted to engage a bone;
 a housing at a proximal end of said bone anchor;
 a longitudinal bore in said housing;
 said bore being aligned with the bone screw and having an open end and a closed end;
 a hemispherical pocket at the closed end of said bore;
 a deflectable post having a proximal end, an elongated body and a distal end;
 the proximal end of said deflectable post extending from the open end of said longitudinal bore;
 a spherical retainer at the distal end of the deflectable post;
 the spherical retainer being received in the hemispherical pocket of the bore;
 a fastener which secures the spherical retainer in the hemispherical pocket and allows the deflectable post to pivot and rotate relative to the bone anchor; and
 a spring positioned within the bore between the deflectable post and the housing such that the spring flexibly resists pivoting of the deflectable post towards the housing.

17. The spine stabilization device of claim 16, further comprising:
a limit surface associated with to the housing and positioned to contact the deflectable post after a first angle of pivoting of the deflectable post away from alignment with the bone screw; and
wherein the limit surface resists further pivoting of said deflectable post beyond said first angle.

18. The spine stabilization device of claim 16, further comprising:
a limit surface associated with the housing and positioned to contact the deflectable post after a first angle of pivoting of the deflectable post away from alignment with the bone screw; and
wherein deflection of the proximal end of the deflectable post after contact between the deflectable post and the limit surface requires at least double the load per unit of deflection than deflection of said post prior to contact between the deflectable post and the limit surface.

19. The spine stabilization device of claim 16, wherein said spring is made of PEEK.

20. The spine stabilization device of claim 16, wherein the spring comprises a first portion in contact with the deflectable post, a second portion in contact with the housing and a flexible portion between the first portion and the second portion which is elastically deformed by pivoting of the deflectable post towards the housing.

21. The spine stabilization device of claim 16, wherein the spring comprises a first portion in contact with the deflectable post, a second portion in contact with the housing and a flexible portion between the first portion and the second portion which is elastically deformed by pivoting of the deflectable post towards the housing and wherein a third portion comprises a plurality of lever arms.

22. The spine stabilization device of claim 16, wherein the spring comprises a first portion in contact with the deflectable post, a second portion in contact with the housing and a flexible portion between the first portion and the second portion which is elastically deformed by pivoting of the deflectable post towards the housing and wherein the third portion comprises a coil.

23. The spine stabilization device of claim 16, wherein the spring comprises one or more spring washers.

24. The spine stabilization device of claim 16, wherein the spring is radially compressed by deflection of the deflectable post.

25. An implantable spine stabilization device comprising:
an elongated bone anchor having a distal end and a proximal end;
a post having a distal end and a proximal end;
a ball-joint which secures the distal end of the post to the proximal end of the bone anchor such that the post can pivot relative to the bone anchor;
a tubular extension of the bone anchor which extends over a distal portion of the post; and
a spring disposed between the distal portion of the post and the tubular extension of the bone anchor whereby the spring biases the post into alignment with the bone anchor.

26. The spine stabilization device of claim 25, further comprising:
a limit surface associated with the tubular extension housing and positioned to contact the post when the post pivots through a first angle from alignment with the bone anchor; and
wherein the limit surface resists pivoting of said post beyond said first angle.

27. The spine stabilization device of claim 25, wherein said spring has a ring having an outer diameter sized to fit with the tubular extension and a central aperture sized to receive the post wherein the central aperture is substantially surrounded by a plurality of lever arms connected to the ring.

28. The spine stabilization device of claim 25, wherein said spring is made of PEEK.

29. The spine stabilization device of claim 25, wherein said spring comprises one or more planar spring elements.

30. The spine stabilization device of claim 26, wherein said spring comprises a flexible coil.

* * * * *